US010373467B2

(12) United States Patent
Devdas et al.

(10) Patent No.: US 10,373,467 B2
(45) Date of Patent: *Aug. 6, 2019

(54) METHOD FOR DEFINING ACCESS PERIMETERS AND HANDLING PERIMETER BREACH EVENTS BY RESIDENTS OF AN ASSISTED LIVING FACILITY

(71) Applicant: PHILIPS NORTH AMERICA LLC, Andover, MA (US)

(72) Inventors: Vikram Devdas, Vancouver (CA); Shane McNamara, Vancouver (CA); Christopher Pang, Vancouver (CA); Richard Heaton, Vancouver (CA); Niall Walsh, Vancouver (CA)

(73) Assignee: PHILIPS NORTH AMERICA LLC, Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/954,547

(22) Filed: Apr. 16, 2018

(65) Prior Publication Data

US 2018/0322759 A1 Nov. 8, 2018

Related U.S. Application Data

(63) Continuation-in-part of application No. 15/880,070, filed on Jan. 25, 2018, now Pat. No. 10,198,927, (Continued)

(51) Int. Cl.
*G08B 21/02* (2006.01)
*G08B 21/04* (2006.01)
(Continued)

(52) U.S. Cl.
CPC .......... *G08B 21/043* (2013.01); *A61B 5/0024* (2013.01); *G08B 21/0261* (2013.01);
(Continued)

(58) Field of Classification Search
CPC .. G06F 19/00; G06F 19/3418; G06F 19/3481; G06F 3/167; G06F 19/328;
(Continued)

(56) References Cited

U.S. PATENT DOCUMENTS 6,182,408 B1 * 2/2001 Poehler .................... E04H 1/02
52/200
6,688,052 B1 * 2/2004 Flanders ................ E04H 1/005
52/169.2
(Continued)

*Primary Examiner* — Daniel Previl

(57) ABSTRACT

One variation of a method for detecting breach events by residents of an assisted living facility includes: defining an access perimeter containing a first space and excluding a second space within a facility, the first space and the second space separated by a door; assigning the first individual access perimeter to a first resident, in a set of residents, occupying the facility; maintaining the door in an unlocked state by default during a first period of time; tracking locations of resident wearable devices associated with residents, in the set of residents, within the facility during the first period of time; and, in response to a first location of a first resident wearable device associated with the first resident falling inside the individual access perimeter and within a threshold distance of the door at a first time during the first period of time, triggering the door to enter a locked state.

20 Claims, 8 Drawing Sheets

Related U.S. Application Data which is a continuation of application No. 15/339,771, filed on Oct. 31, 2016, now Pat. No. 9,922,524.

(60) Provisional application No. 62/485,637, filed on Apr. 14, 2017, provisional application No. 62/249,060, filed on Oct. 30, 2015.

(51) Int. Cl.

| | | |
|---|---|---|
| *H04W 4/02* | (2018.01) | |
| *G08B 25/00* | (2006.01) | |
| *A61B 5/00* | (2006.01) | |
| *G16H 10/60* | (2018.01) | |
| *G16H 40/63* | (2018.01) | |
| *A61B 5/103* | (2006.01) | |
| *A61B 5/11* | (2006.01) | |
| *G06Q 50/22* | (2018.01) | |
| *G06Q 50/26* | (2012.01) | |
| *G08B 21/00* | (2006.01) | |
| *G08B 21/08* | (2006.01) | |
| *G08B 21/22* | (2006.01) | |

(52) U.S. Cl.
CPC ..... *G08B 21/0423* (2013.01); *G08B 21/0446* (2013.01); *G08B 25/005* (2013.01); *H04W 4/023* (2013.01); *A61B 5/00* (2013.01); *A61B 5/0002* (2013.01); *A61B 5/0015* (2013.01); *A61B 5/103* (2013.01); *A61B 5/11* (2013.01); *G06Q 50/22* (2013.01); *G06Q 50/265* (2013.01); *G08B 21/00* (2013.01); *G08B 21/02* (2013.01); *G08B 21/0272* (2013.01); *G08B 21/0286* (2013.01); *G08B 21/0461* (2013.01); *G08B 21/0492* (2013.01); *G08B 21/088* (2013.01); *G08B 21/22* (2013.01); *G16H 10/60* (2018.01); *G16H 40/63* (2018.01)

(58) Field of Classification Search
CPC ............. G06F 19/3475; G06F 21/6245; G06F 3/04847; G08B 21/0446; G08B 21/043; G08B 21/02; G08B 25/016; G08B 21/0461; G08B 25/00; G08B 25/009; G08B 25/014; G08B 25/10; G08B 25/14; G08B 21/0469; G08B 21/0476; G08B 21/0492; G08B 21/00; G08B 21/0261; G08B 21/0272; G08B 25/005; G08B 13/19608; G08B 19/00; G08B 21/22; G08B 25/001; G08B 29/186; G06Q 50/22; G06Q 50/24; G06Q 10/10; G06Q 50/265; G06Q 10/06; G06Q 10/087; G06Q 40/08; G10L 15/22; G16H 10/20; G16H 40/20; G16H 10/60; G16H 40/63; G16H 10/65; G16H 40/67; G16H 20/30; G16H 50/20; G16H 50/30; G01S 1/70; G01S 5/16; G01S 3/7865; G06K 9/20; G06K 9/00255; G06K 9/00288; G06K 9/00771; G06K 9/00348; A61B 5/1117; A61B 5/0022; A61B 2560/0242; A61B 5/00; A61B 5/0002; A61B 5/0015; A61B 5/0024; A61B 5/103; A61B 5/11; A61B 5/1113; A61B 5/747; A61B 2503/08; A61B 2562/0219; A61B 2562/046; A61B 5/1112; A61B 5/1127; A61B 5/1128; A61B 5/6822; A61B 5/6824; A61B 5/6829; A61B 5/6889; A61B 2503/40; A61B 5/01; A61B 5/02055; A61B 5/02438; A61B 5/0816; A61B 5/7264; A61B 5/741; A61B 5/7475; A61B 5/749; H04W 4/023; H04W 4/90; H04W 76/50; A47G 29/08; A61G 12/00; A61G 5/1094; G07C 9/00079; H04M 11/04; H04M 2242/04; H04N 7/141; H04N 7/181; H04N 7/185; A01K 11/008; A01K 27/001; A01K 27/009; A01K 29/005; G01P 13/00; G01P 15/18; G01P 21/00; G01P 3/00; G09B 19/00; G09B 19/0038
USPC ...... 340/539.13, 573.1, 562, 539.12, 539.22, 340/545.1, 545.8, 545.9, 545.7, 572.9
See application file for complete search history.

(56) References Cited

U.S. PATENT DOCUMENTS

| | | | |
|---|---|---|---|
| 2003/0229512 A1* | 12/2003 | Lenhard, II | G06Q 10/10 705/2 |
| 2006/0267780 A1* | 11/2006 | Adams | A61B 5/1113 340/573.1 |
| 2009/0272048 A1* | 11/2009 | Amidon, II | E04H 3/08 52/106 |
| 2012/0153783 A1* | 6/2012 | Shoenfeld | A61L 2/10 312/209 |
| 2013/0100268 A1* | 4/2013 | Mihailidis | G08B 21/02 348/77 |
| 2015/0106105 A1* | 4/2015 | Clough | G07C 9/00126 704/275 |

* cited by examiner

METHOD FOR DEFINING ACCESS PERIMETERS AND HANDLING PERIMETER BREACH EVENTS BY RESIDENTS OF AN ASSISTED LIVING FACILITY

CROSS-REFERENCE TO RELATED APPLICATIONS

This application claims the benefit of U.S. Provisional Patent Application No. 62/485,637, filed on 14 Apr. 2017, which is incorporated in its entirety by this reference.

The application is a continuation-in-part application of U.S. patent application Ser. No. 15/880,070, filed on 25 Jan. 2018, which is a continuation of U.S. patent application Ser. No. 15/339,771, filed on 31 Oct. 2016, which claims the benefit of U.S. Provisional Patent Application No. 62/249,060, filed on 30 Oct. 2015, all of which are incorporated in their entireties by this reference.

TECHNICAL FIELD

This invention relates generally to the field of senior and disabled care and more specifically to a new and useful method for customizing access perimeters and handling perimeter breach events by residents of an assisted living facility in the field of senior and disabled care.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
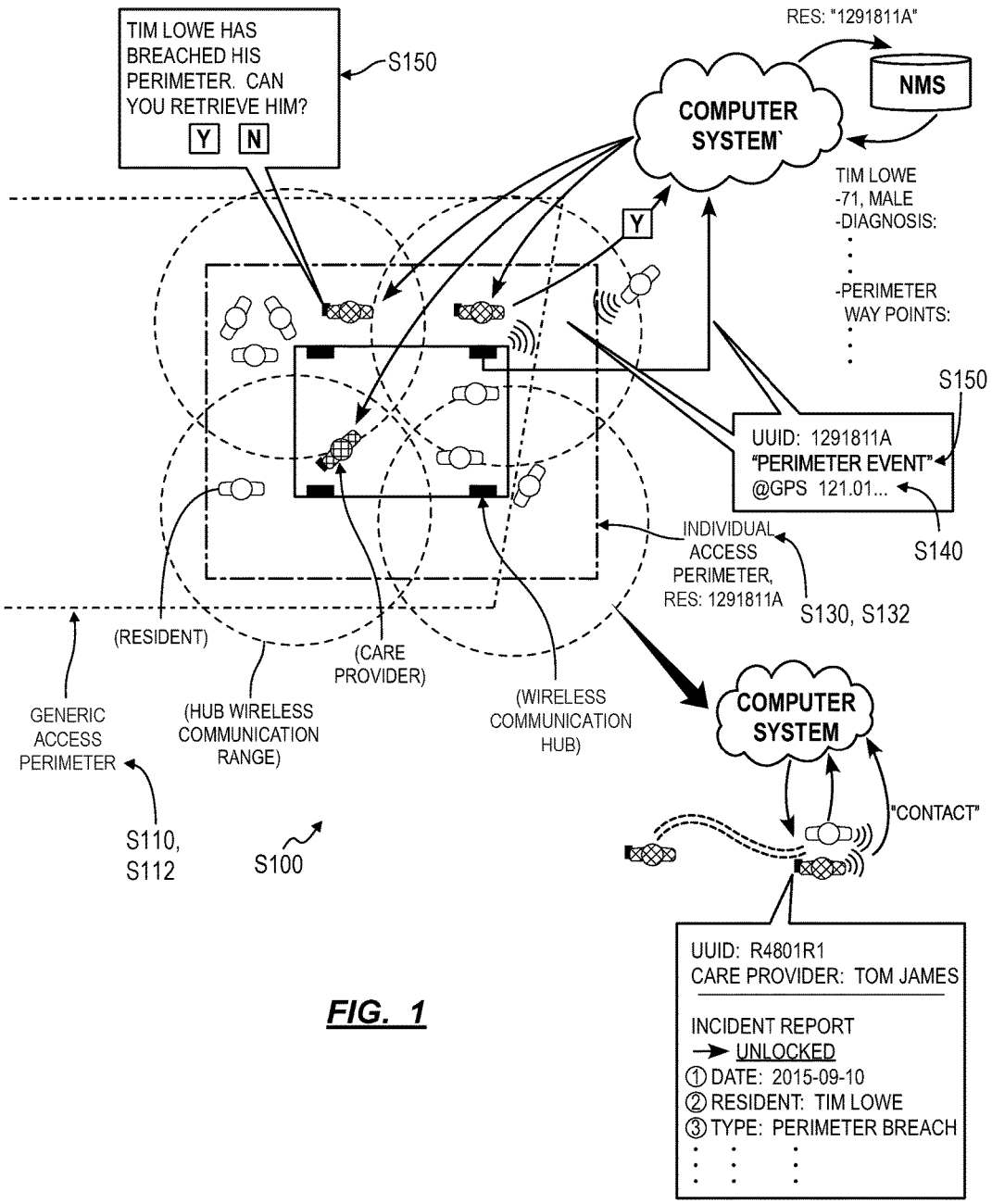
FIG. 1 is a flowchart representation of a method.
Figure 4A:
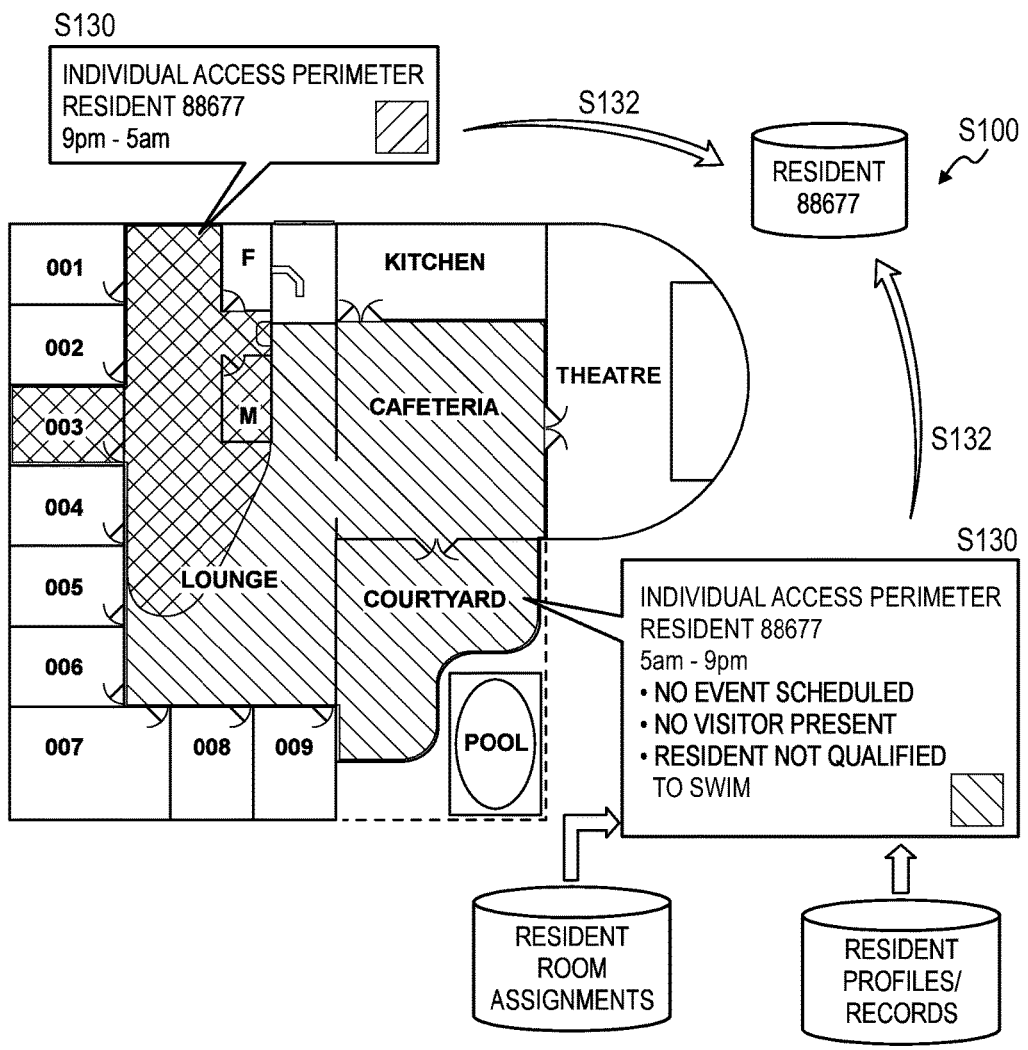
FIGS. 4A, 4B, and 4C are schematic representations of variations of the method S100.
Figure 4B:
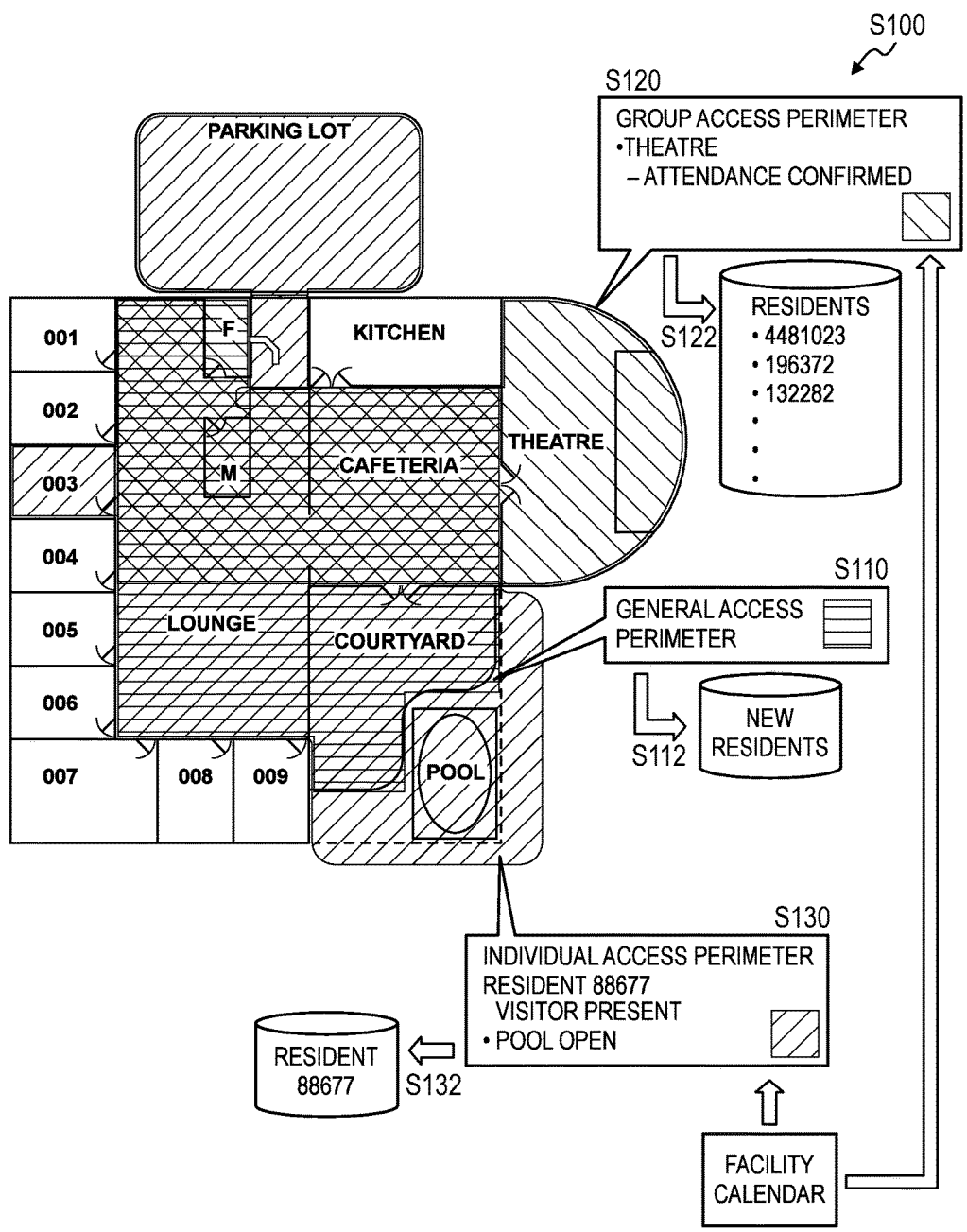

As shown in FIGS. 1 and 4B, a method S100 for detecting perimeter breach events by residents of an assisted living facility includes: defining a generic access perimeter within a facility in Block S110; assigning the generic access perimeter to residents in a set of residents occupying the facility in Block S112; defining a first individual access perimeter excluding a first portion of the generic access perimeter in Block S130; assigning the first individual access perimeter to a first resident, in the set of residents, in Block S132; tracking locations of resident wearable devices associated with residents, in the set of residents, within the facility in Block S140; in response to a first location of a first resident wearable device associated with the first resident falling outside of the first individual access perimeter at a first time, distributing a first breach event prompt to assist the first resident, proximal the first location, to care provider mobile devices associated with care providers affiliated with the facility in Block S150; and, in response to a second location of a second resident wearable device—associated with a second resident in the set of residents—falling outside of the generic access perimeter assigned to the second resident at a second time, distributing a second breach event prompt to assist the second resident proximal the second location to care provider mobile devices associated with care providers affiliated with the facility in Block S150.

Figure 4C:
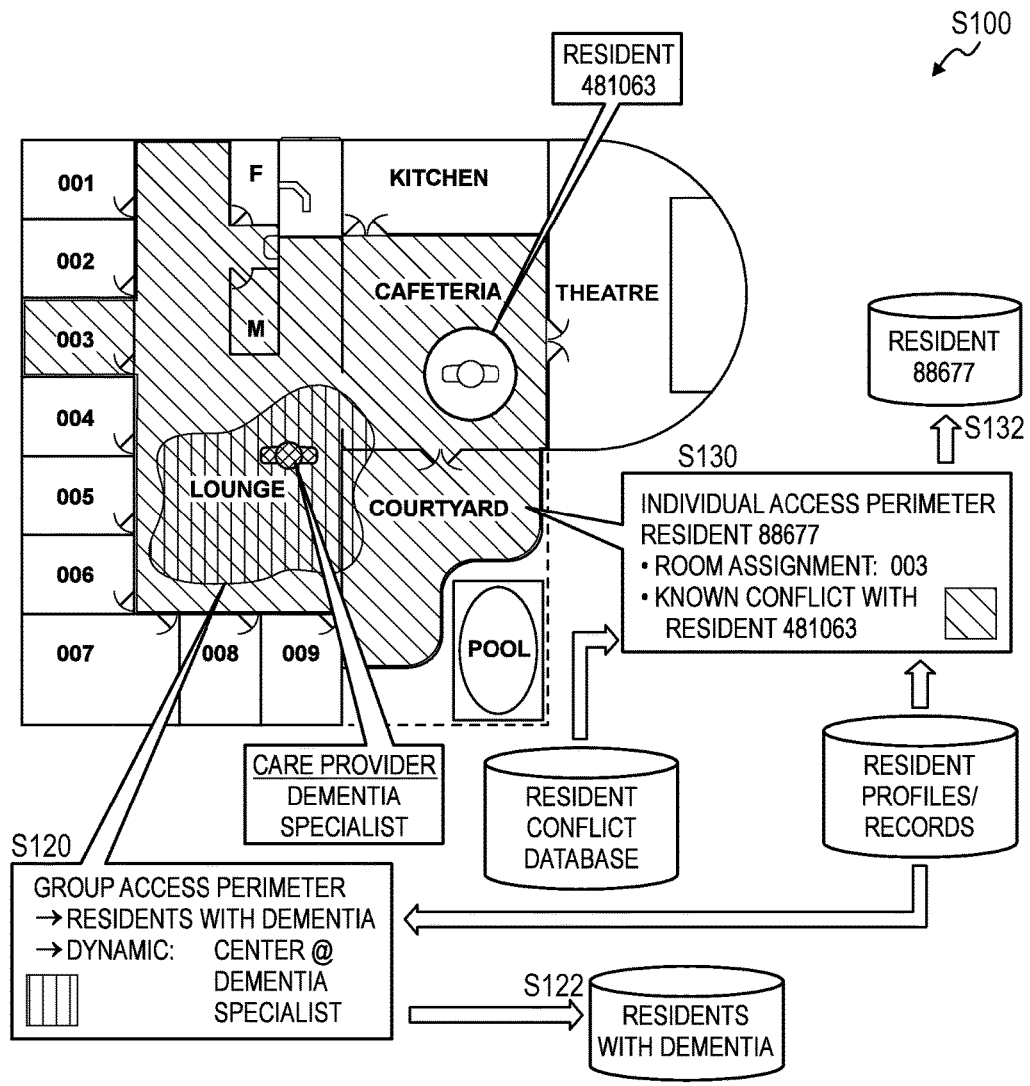

As shown in FIG. 4C, one variation of the method S100 includes: defining a generic access perimeter within a facility in Block S110; assigning the generic access perimeter to residents, in a set of residents occupying the facility, by default in Block S112; identifying a first resident group comprising residents, in the set of residents, characterized by a first characteristic in Block S120; defining a first group access perimeter excluding a first portion of the generic access perimeter based on the first demographic in Block S120; assigning the first group access perimeter to residents in the first resident group in Block S122; defining a second individual access perimeter excluding a second portion of the generic access perimeter based on a second characteristic of a second resident, in the set of residents, in Block S130; assigning the second individual access perimeter to the second resident in Block S132; tracking locations of resident wearable devices associated with residents, in the set of residents, within the facility in Block S140; in response to a first location of a first resident wearable device associated with a first resident, in the first resident group, falling outside of the first group access perimeter at a first time, distributing a first breach event prompt to assist the first resident, proximal the first location, to care provider mobile devices associated with care providers affiliated with the facility in Block S150; and, in response to a second location of a second resident wearable device associated with the second resident falling outside of the second individual access perimeter at a second time, distributing a second breach event prompt to assist the second resident proximal the second location to care provider mobile devices within the facility in Block S150.

As shown in FIGS. 4A, 4B, and 4C, another variation of the method S100 includes: defining a first access perimeter within a facility in Block S130; assigning the first access perimeter to a first resident, in a set of residents in the facility, in Block S132; tracking locations of resident wearable devices associated with residents, in the set of residents, within the facility in Block S140; disabling a first subregion within the first access perimeter coincident a second location of a second resident, in the set of residents, flagged for separation from the first resident in Block S132; and, in response to a first location of a first resident wearable device associated with the first resident falling outside of the first access perimeter, distributing a first breach event prompt to assist the first resident, proximal the first location, to care provider mobile devices associated with care providers affiliated with the facility in Block S150.

2. Applications

Generally, the method S100 can be implemented within or in cooperation with an assisted living facility to provide real-time prompts to care providers in support of care for residents of the assisted living facility. In particular, a computer system implementing Blocks of the method S100 can interface with wearable devices assigned to residents of the facility to detect instances in which residents of the assisted living facility move beyond generic, group-specific, or custom individual access perimeters within and around the facility assigned to these residents (hereinafter "perimeter breach events"). The computer system can respond to these events by transmitting notifications containing perimeter breach event details to mobile devices carried by care providers within the facility substantially in real-time as residents intentionally or unintentionally breach their assigned access perimeters, thereby enabling these care providers to rapidly identify and then return these residents to their permitted areas within the facility.

2.1 Examples

In one example shown in FIG. 4B, upon first arrival at the facility, a wearable device can be assigned to a resident, and the computer system (or an administrator at the facility) can assign a generic access perimeter—including common public interior spaces within the facility and excluding administrator offices and food preparation areas—to the resident's wearable device. The computer system can then immediately track the resident within the facility and issue prompts if the resident moves beyond this generic access perimeter. If the it is determined that the exhibits a low flight risk, the computer system can associate the resident with a like group of other low-risk residents and assign the resident a group access perimeter that extends to unenclosed exterior spaces in the facility. However, if the computer system (or the administrator) determines that the resident is exhibiting or has been diagnosed with dementia, such as in an health record of the resident, the computer system can instead associate the resident with a like group of other high-risk residents and assign the resident a group access perimeter that includes some common interior space within the facility but excludes unenclosed exterior spaces, an exercise facility, and a kitchen except when a mobile device assigned to a care provider falls within a preset supervision distance (e.g., ten meters) of the resident's wearable device or is otherwise present in these restricted spaces. In this example, the computer system can thus assign a generic access perimeter to a new resident, group the new resident with other residents based on similar characteristics or medical conditions, and can selectively reassign a group-specific access perimeter to this resident accordingly, such as automatically or with the supervision of an administrator or care provider in the facility.

The computer system can also dynamically adjust and update the generic, group, and individual access perimeters assigned to residents of the facility over time in order to provide these residents with selective access to different areas within and around the facility over time. For example, the computer system can: assign a generic access perimeter, including both interior and exterior public common spaces, to many residents of the facility during daytime hours (e.g., from 5 AM to 9 PM); define an individual access perimeter for each resident in the facility, wherein an individual access perimeter for one resident is reduced to the resident's room, a nearest bathroom, and a path therebetween; and reassign these individual access perimeters to corresponding residents during nighttime hours (e.g., from 9 PM to 5 AM), as shown in FIG. 4A. In this example, the computer system can thus: track residents both during daytime and nighttime hours; issue prompts to care provider mobile devices to assist residents who have moved beyond the generic access perimeter during daytime hours, thereby reducing opportunity for residents to escape the facility—intentionally or unintentionally—unnoticed while also providing a greater sense of freedom to these residents who may feel less oppressed by constant oversight from care providers; and issue prompts to care provider mobile devices to assist residents who have moved beyond their individual access perimeters during nighttime hours, thereby enforcing a curfew within the facility and enabling care providers to rapidly identify and address residents wandering at night, all without physical barriers or locked doors that may otherwise breed distrust or discomfort for residents in the facility.

In another example, the computer system can: default to assigning a generic access perimeter to residents in the facility; generate an individual access perimeter by shrinking the generic access perimeter (e.g., by five meters or by 5%) for a particular resident who has been involved in an above-average rate of perimeter breach events in the past; and reassign this individual access perimeter to the particular resident. Similarly, if the computer system determines that this particular resident exhibits a pattern of breaching the generic access perimeter via a particular door of the facility, the computer system can define an individual access perimeter that removes an area of the generic access perimeter around this door (e.g., within a ten-meter radius of this door) and assign this individual access perimeter to the particular resident; thus when the particular resident approaches this door in the future, the computer system can issue a prompt in real-time to a nearby care provider to observe and/or to retrieve the particular resident prior to the particular resident passing through the door.

In yet another example shown in FIG. 4B, the computer system can: define a temporary individual access perimeter that extends beyond a current generic access perimeter, such as to include the entirety of the grounds of the facility; assign this individual access perimeter to a particular resident during an on-site visit by a visitor (e.g., a family member, a friend); and return the particular resident to the generic access perimeter or to another access perimeter of reduced area once the visitor leaves the facility.

In another example shown in FIG. 4C, the computer system dynamically adjusts an individual access perimeter assigned to a first resident to exclude an area (e.g., a five-meter-diameter restriction zone) around a second resident with whom the first resident has quarreled in the past based on tracked locations of resident wearable devices assigned to these residents over time. Thus, when the location of the first resident's wearable device enters a restriction zone defined around the second resident, the computer system can issue a prompt in real-time to a nearby care provider to supervise or separate the first and second residents.

In the foregoing examples, the computer system can track the location of each resident of the facility—such as at a rate of once per five-second interval or at a rate proportional to each resident's speed of motion throughout the facility—through wearable devices worn by these residents. Upon receipt of locations of resident wearable devices, the computer system can compare these wearable device locations to generic, group, and/or individual access perimeters assigned to corresponding residents to identify specific resident's who have moved beyond their assigned boundaries within or around the facility. The computer system can then selectively notify care providers on duty within the facility of such breach events in (near) real-time, such as by serving prompts or notifications through mobile device s (e.g., smartphones, tablets, or wearable devices) carried by these care providers.

2.2 Computer System

For each resident in a facility, the computer system can therefore bound the resident to: one campus; one building or cluster of buildings within the campus; or one room or cluster of rooms within one building on the campus; etc. such as a function of the resident's characteristics, medical history, escape risk, and/or interactions with other residents and/or as a function of time of day, events at the facility, and/or presence of visitors, etc. In particular, the computer system can bound a resident to locations within the facility that limit risk of the resident escaping the facility, limit risk of physical harm to the resident, and/or limit risk of emotional harm to the resident.

Blocks of the method S100 can be executed by a computer system, such as on a local computer system within an assisted living facility (e.g., a local server), by a remote server in the cloud, or by a distributed computer network (hereinafter "computer system"). In particular, the computer system can interface with multiple devices—including resident wearable devices, care provider mobile devices, and/or wireless communication hubs—within and around the assisted living facility (hereinafter the "facility") to handle and respond to perimeter breach events for residents of the facility.

The method S100 is described herein as implemented within or in conjunction with an assisted living facility. However, the method S100 can be similarly implemented within a general hospital, a psychiatric hospital, a preschool, a summer camp, or any other health institution, clinic, or community. Similarly, the method S100 is described below as implemented by a facility to serve a resident of the facility, though the method S100 can additionally or alternatively be implemented to serve a patient at a general hospital, a student at a school, or a child at a day care or summer camp, etc. The method S100 can be similarly implemented by a facility to guide a care provider—such as a nurse, a teacher, or a camp counselor—to serve such residents, patients, or students, etc.

3. Devices

Figure 2:
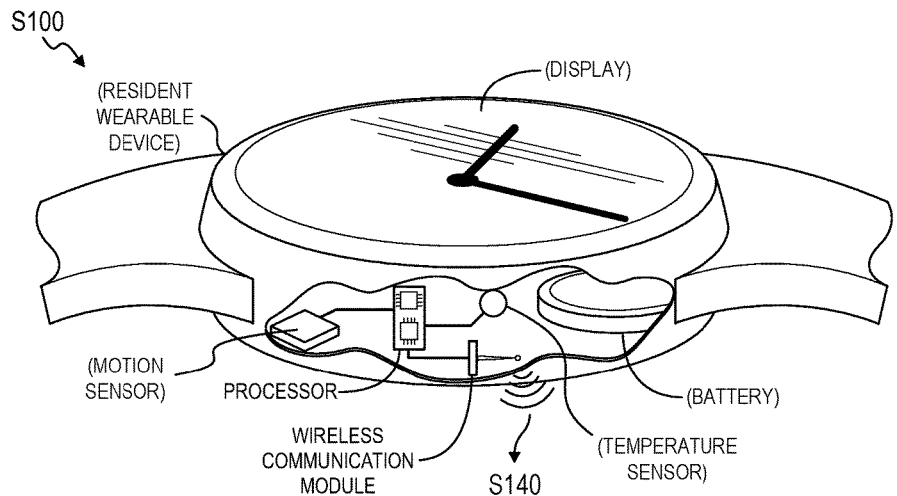
FIG. 2 is a schematic representation of a resident wearable device.
Figure 3:
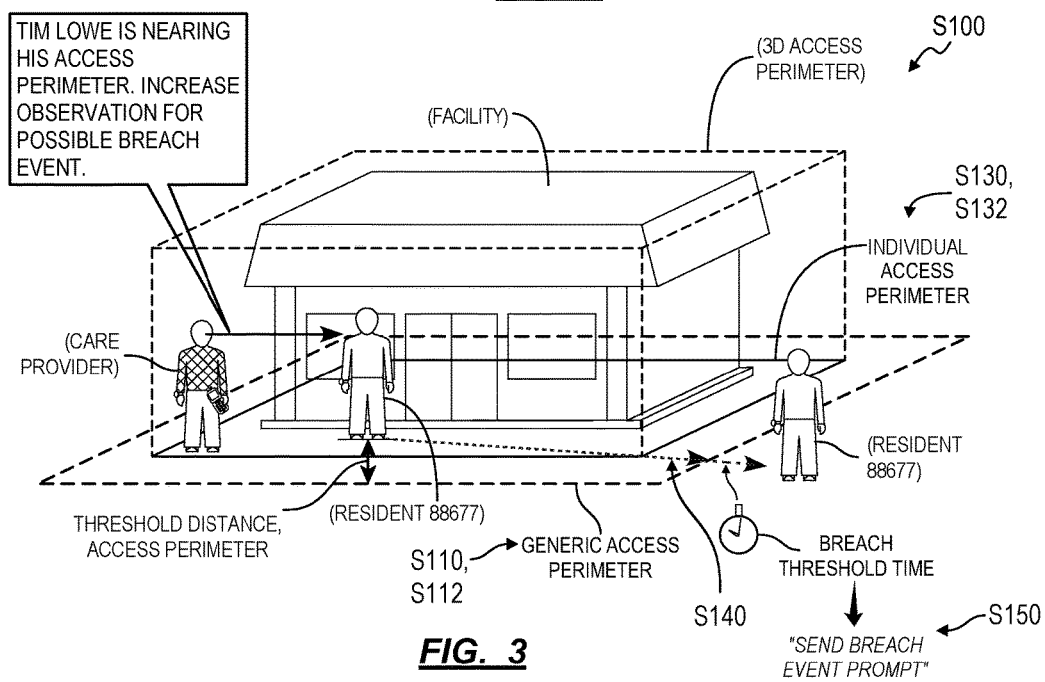
FIG. 3 is a flowchart representation of one variation of the method.

As shown in FIGS. 1, 2, and 3, Blocks of the method S100 can be executed by a local or remote computer system that interfaces with a set of wearable devices assigned to a group of residents and to a group of care providers, one or more wireless communication hubs within or around an assisted living facility, and/or a set of mobile devices assigned to the group of care providers.

In one implementation, an administrator of the assisted living facility (hereinafter "facility") can access an administrator interface to assign a resident of the facility one or more (i.e., a set of) resident wearable devices. In one example, the administrator assigns a resident two wearable devices, including: a first wearable device to be worn by the resident during the day and recharged at night; and a second wearable device to be worn by the resident at night and recharged during the day. Alternatively, care providers in the facility can exchange a resident wearable device worn by a resident with a recharged resident wearable device on a regular interval, such as once per week or once per month and relink the resident's profile or account at the facility with an identify of her assigned wearable device.

Each resident wearable device can thus be loaded with a unique ID (e.g., a UUID), and the unique ID can be associated with a particular resident of the facility, such as in a name mapping server (or "NMS"), as shown in FIG. 1. In this implementation, the resident wearable device can include: a set of inertial sensors; a processor configured to classify its motion (e.g., sleeping, sitting, walking, running, and a rate of each) based on outputs of the inertial sensor(s); a geospatial location sensor (e.g., a GPS sensor); a wireless communication module that broadcasts location data; and/or a rechargeable battery that powers the foregoing elements, as shown in FIG. 3.

(In the foregoing implementation, the administrator of the assisted living facility can assign or otherwise provide a care provider—employed by the facility—with one or more care provider mobile devices. A care provider mobile device can be substantially similar to the resident wearable device, as described above.)

As shown in FIG. 2, a resident wearable device can additionally or alternatively include: a short-range wireless communication module (e.g., a low power 2.4 GHz wireless communication device); an inertial sensor (e.g., an accelerometer); an input field (e.g., a touchscreen); a processor; and/or a rechargeable battery. The processor can implement "proximity card" methods to confirm that the care provider has made contact with the resident based on outputs of the inertial sensor, such as when a care provider taps his wearable device to a wearable device worn by a resident during or after responding to a perimeter breach event, as described below. Each care provider mobile device can also be assigned and can store in local memory a unique ID (e.g., a UUID), and each care provider mobile device ID can be associated with a particular care provider at the facility, such as in a NMS. A care provider mobile device ID can also be associated with a set of information corresponding to a care provider assigned to the care provider mobile device, such as the care provider's name, facility ID, gender, age, specialty (e.g., manual assistance, nurse, physical therapist, pharmacist, doctor, administrator), etc. Furthermore, a care provider mobile device can include a digital user interface (e.g., a display); the care provider mobile device can render a prompt to respond to a perimeter breach event and can receive a response to this prompt from a corresponding care provider through the display, as shown in FIG. 1.

As shown in FIG. 1, a mobile device (e.g., a tablet or a smartphone) assigned to a care provider can execute a native care provider application, as described below. For example, the native care provider application can: receive an event prompt from a local or remote server; alert a care provider of the event prompt through a user interface (e.g., on an integrated display); receive a response to the event prompt (e.g., "Yes, I will respond" or "No, I cannot respond right now") from the care provider through the user interface; upload the event prompt responses to the remote server; serve an incident report to the care provider through the interface; collect data entered into the incident report manually by the care provider; and communicate these data back to the server.

Additionally or alternatively, an instance of the native care provider application can be installed on a private mobile device owned by a care provider, such as the care provider's personal smartphone or tablet.

4. Resident Location

Figure 5:
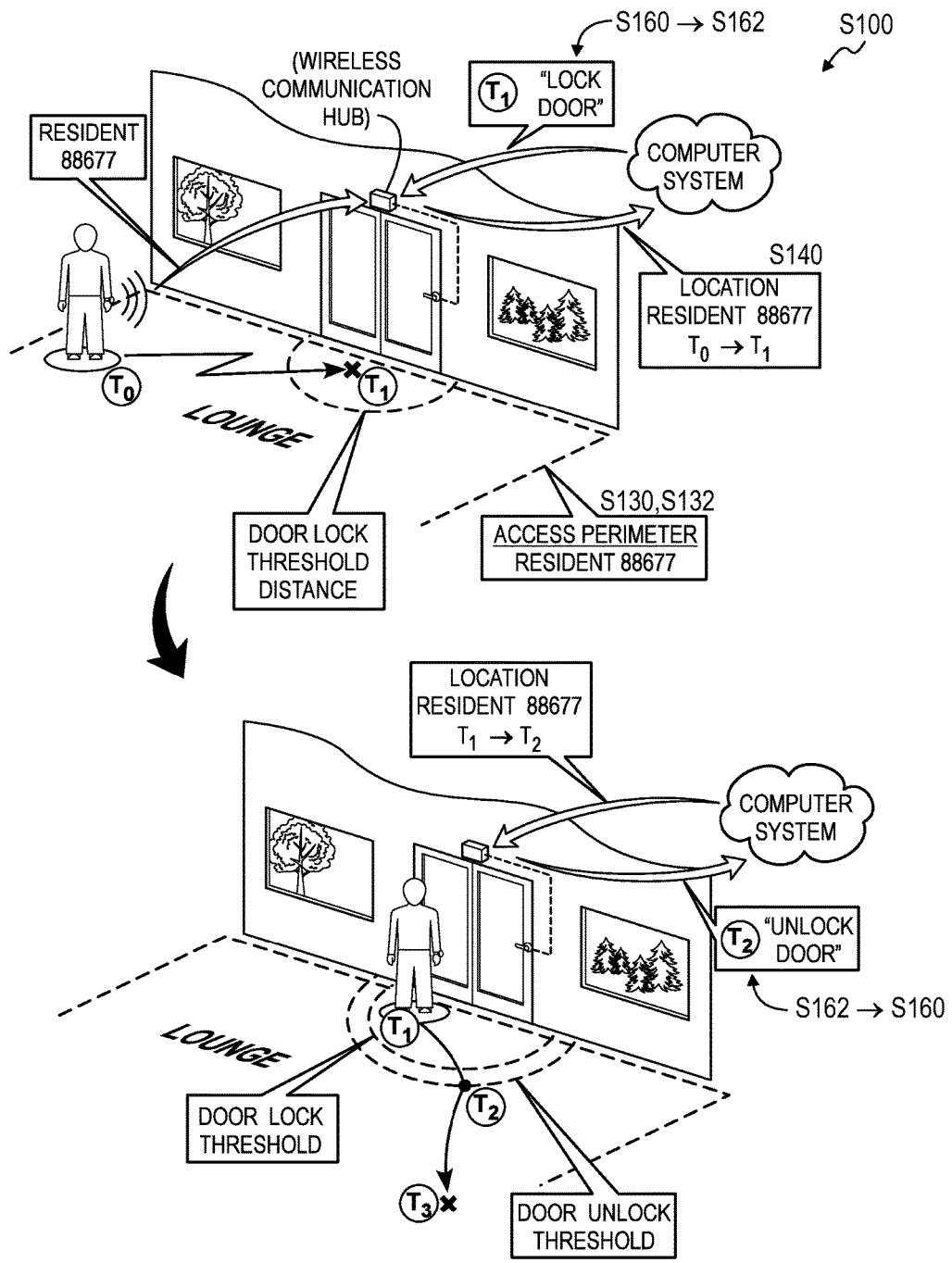
FIG. 5 is a flowchart representation of one variation of the method.

Block S140 of the method S100 recites tracking a location of a first resident wearable device associated with the first resident. Generally, in Block S140, the computer system cooperates with the resident's wearable device, one or more local wireless communication hubs, and/or any other device within proximity of the resident's wearable device to determine the location of a resident. In particular, the computer system can regularly determine a location—such as an absolute geospatial location of the resident, a location relative to one or more wireless communication hubs within the facility, or a location relative to a virtual coordinate system defined for the facility—of each resident wearable device and each care provider mobile device deployed throughout the facility in Block S140. For example, the computer system can: track locations of a resident wearable device based on wireless communications between the resident wearable device and a set of wireless communication hubs distributed throughout the facility, as shown in FIGS. 1 and 5; and then detect breach events involving the corresponding resident based on differences between these locations and an access perimeter assigned to this resident, as described below.

In one implementation, in response to detecting a fall event, the resident's wearable device can regularly broadcast a test signal to one or more local wireless communication hubs of known location(s) within the facility. The resident wearable device can then receive return signals and wireless IDs (e.g., UUIDs) from the wireless communication hub(s), calculate a flight time for the test signal, and transmit these wireless IDs and corresponding flight times of the test signals (via a local wireless hub) to the computer system, which can then reconstruct the location of the resident's wearable device—and therefore the resident—from these data. For example, if a single wireless communication hub is within wireless range of the resident's wearable device, the computer system can determine that the resident is within a circular area centered at the known location of the wireless communication hub by: referencing the UUID received from the wireless communication hub to a map of the facility; and calculating the radius of the circular area based on the flight time of a test signal broadcast by the wearable device and then received from the wireless communication hub. In this example, the computer system can: project an area defined by the circular area to the access perimeter assigned to the resident; determine that the resident has breached her assigned access perimeter if any or at least a threshold proportion (e.g., 50%) of the projected area falls outside of the access area; and transmit a perimeter breach event prompt to care providers on duty throughout the facility accordingly, such as including a map indicating the current position of the resident within the facility, in Block S150.

In the foregoing implementation, the resident wearable device can also: collect UUIDs and test signal flight times from two or more local wireless communication hubs; and transmit these UUIDs and test signal flight times to the computer system via a local wireless communication hub. The computer system can then implement similar techniques to determine the location of the resident within the facially, such as by triangulating the position of the resident's wearable device within the facility relative to the three (or more) wireless communication hubs. The computer system can also triangulate the resident's wearable device based on proximity to other devices within the facility, such as based on flight times of test signals broadcast by the resident's wearable device and returned from other resident wearable devices and/or care provider mobile devices within the facility. The computer system can then: determine that the resident has breached her assigned access perimeter if the specific location of the resident falls outside of the access area; and transmit a perimeter breach event prompt to care providers on duty throughout the facility accordingly in Block S150.

In the foregoing implementations, the computer system can determine the location (e.g., a point, an area) of the resident's wearable device based on time of flight data received from one or more wireless communication hubs and/or other wireless-enabled devices in communication with the resident's wearable device (e.g., a mobile device associated with the resident and communicatively coupled to the resident wearable device) regularly during operation. For example, the computer system can cooperate with the resident's wearable device to implement a static location tracking rate, such as once per minute or once per five-second interval. Alternatively, the computer system and resident wearable device can implement a dynamic location tracking rate. For example, a controller integrated into the resident wearable device can predict the user's current activity—such as sleeping, sitting, walking, or running, etc.—based on outputs of motion and/or inertial sensors integrated into the wearable device. When the resident is determined to be sleeping or sitting, the wearable device can broadcast a wireless signal—which may be collected by local wireless communication hubs and transformed into a location of the wearable device by the computer system—at a rate of once per five-minute interval. When the resident is determined to be walking slowly, the wearable device can broadcast a wireless signal at a rate of once per ten-second interval; as the resident's speed of motion increases, the wearable device can increase its broadcast rate, such as up to a maximum broadcast rate of once per five-second interval. Furthermore, once the resident is determined by the computer system to have breached her assigned access perimeter in Block S150, the computer system can transmit a command to increase the broadcast rate to 1 Hz to the wearable device (e.g., via a local wireless communication hub).

However, the resident's wearable device, the wireless communication hub(s), and/or the computer system can cooperate in any other way to determine the location of the resident's wearable device. The resident's wearable device, the wireless communication hub(s), and/or the computer system can repeat these processes over time to track the location of the resident throughout the facility. In particular, the computer system can regularly cooperate with the resident's wearable device and/or wireless communication hubs distributed throughout the facility to track the resident's location; the computer system can then dynamically adjust the resident's individual access perimeter and selectively issue alarms for breach events based on these location data.

The computer system can implement similar methods and techniques to track locations of other wearable devices assigned to and worn by other residents of the facility over the same period of time and to track locations of mobile devices carried or worn by care providers active with the facility.

5. Generic Access Perimeter

Block S110 of the method S100 recites defining a generic access perimeter within a facility; and Block S112 of the method S100 recites assigning the generic access perimeter to each resident in a set of residents occupying the facility. Generally, the computer system: defines a generic perimeter for residents of the facility automatically or in cooperation with an administrator of the facility in Block S110; associates this generic access perimeter with residents in the facility in Block S112; and then triggers an alarm in Block S150 if a resident of the facility moves beyond this generic access perimeter.

In one implementation, an administrator of the facility accesses an administrator interface hosted by the computer system, such as through a web browser, to select geospatial (e.g., GPS-based) waypoints around the facility from a virtual geospatial map; and the computer system then transforms these waypoints into a polygonal access perimeter within or around the facility, as shown in FIG. 3. In this implementation, the administrator can selectively associate the generic access perimeter with all or a subgroup of residents of the facility. The computer system can cooperate with the administrator to define unique generic access perimeters for various groups of residents occupying the facility.

In a similar implementation, the computer system can: access a vectorized map of the facility and ground around the facility, such as including labeled rooms (e.g., bedrooms, public spaces, bathrooms, kitchens, offices, etc.), interior and exterior doors, courtyards, walking paths, parking lots, and road surfaces. To generate a new generic access perimeter for all or a subgroup of residents in the facility, the computer system can serve the vectorized map of the facility to the administrator through the administrator interface; the administrator can then select rooms from the vectorized map to define accessible spaces within the new generic access perimeter and then assign the new generic access perimeter to all or a subset of residents of the facility. Similarly, the administrator can: define a maximum boundary of the generic access perimeter by selecting a vector representing exterior walls of the facility or by selecting vertices to define a polygonal boundary within the vectorized map; and then select rooms or spaces (e.g., administrator officers, a kitchen, a laundry room) from the vectorized map to remove from the generic access perimeter.

Once a boundary is defined—either automatically or in cooperation with an administrator—the computer system can inset the generic access perimeter from the boundary by a safety offset distance (e.g., two meters), thereby enabling the computer system to preemptively detect a perimeter breach event by a resident as the resident moves toward the boundary and prior to breaching the boundary.

Alternatively, the generic access perimeter can extend to the edge of the boundary, and the computer system can define a pre-alarm zone—within the generic access perimeter—around and inset from the edge of the boundary. In this implementation, the pre-alarm zone can be of a width equal to an accuracy with which the computer system can repeatably determine the location of a resident wearable device, such as two meters for a location accuracy of ± one meter. In this implementation, the computer system can selectively trigger an alarm in Block S150 based on the presence of a wearable device within the pre-alarm zone, the wearable device's approach to the pre-alarm zone, or perimeter breach event histories of the corresponding resident. For example, the computer system can issue a perimeter breach event alarm for a resident once the location of a corresponding wearable device enters the pre-alarm zone if the wearable device approached the boundary of the generic access perimeter at a speed exceeding a threshold and/or if the resident has an history of escape attempts or perimeter breach events. The computer system can implement similar methods and techniques to define a pre-alarm zone for exterior and interior boundaries defined by the generic access perimeter.

However, the computer system can implement any other method or technique to define a generic access perimeter—including an exterior boundary and/or interior boundaries—for various residents of the facility in Block S110.

6. Group Access Perimeter

One variation of the method S100 shown in FIGS. 4B and 4C includes: Block S120, which recites identifying a first resident group comprising residents, in the set of residents, characterized by a first characteristic and defining a first group access perimeter excluding a first portion of the generic access perimeter based on the first demographic; and Block S122, which recites assigning the first group access perimeter to residents in the first resident group. Generally, in Block S120, the computer system can segment a population of residents in the facility into groups, such as based on: resident demographic (e.g., age, gender); resident mobility (e.g., highly-mobile, using a walking, or bound to a wheelchair); known medical conditions (e.g., dementia, diabetes); historical resident cooperation with staff (e.g., highly cooperative versus uncooperative); past breach events involving residents; perceived resident flight risk; and/or past fall events involving residents; etc. The computer system can then implement methods and techniques similar to those described above and below to define a group access perimeter for a group of residents based on common characteristics exhibited by residents in this group, thereby generating a "custom" group access perimeter that accounts for needs and/or risks of residents in this group with greater resolution that the generic access perimeter in Block S120. The computer system can then assign the group access perimeter to each resident in the group and issue a breach event prompt to assist a particular resident in this group when the particular resident's assigned wearable device is detected outside of the group access perimeter.

In one example, the system: defines a generic access perimeter that spans both interior public spaces in the facility and an exterior space around the facility (e.g., a garden, courtyard, or other unbounded outdoor space) in Block S110; and assigns the generic access perimeter to residents in the facility by default in Block S112. Responsive to breach events beyond the generic access perimeter over time at the facility, the computer system can: identify a group of residents (i.e., one or more residents) associated with historical breach events proximal the exterior space (e.g., intended or unintended departures from the facility via this exterior space); define a group access perimeter that spans the same interior public spaces in the facility as the generic access perimeter but that excludes this exterior space; and then assign this group access perimeter to residents in this group.

In another example, the system: identifies a subset of residents—in the population of residents in the facility—diagnosed with dementia, such as indicated in electronic health records stored in a local or remote database; and then aggregate this subset of residents into a resident group. The computer system can then define a group access perimeter: that spans interior common public spaces within the facility, that is offset inside of exterior doors throughout the facility (e.g., by a first offset distance), and that excludes an indoor exercise facility and a kitchen within the facility based on these dementia diagnoses for residents in this group. By assigning the group access perimeter to residents in this group, the computer system can issue breach event prompts when these residents diagnosed with dementia approach exterior doors or enter (or approach) the exercise facility and the kitchen within the facility. In this example, in order to provide care providers in the facility more time to assist residents with dementia, the first offset distance between this group access perimeter and exterior doors of the facility can be greater than offset distances between access perimeters and these same doors for other residents of the facility who are not diagnosed with or who do not exhibit signs of dementia.

In yet another example, the computer system can group the population or residents in the facility into a first group of residents capable of swimming and a second group of residents not capable of swimming in Block S120. In this example, the computer system can define a first group access perimeter that includes a pool area of the facility and a generic access perimeter that excludes the pool area. The computer system can assign the generic access perimeter (or individual variations of the generic access perimeter) to residents of the facility generally. However, during open pool hours at the facility, the computer system can activate the first group access perimeter (or individual variations of the first group access perimeter) for residents in the first group of residents capable of swimming, thereby enabling residents in the first group to access the pool area. The computer system can also: issue breach event prompts for residents who breach the generic access perimeter outside of open pool hours; and issue resident supervision prompts—such as to a care provider present in the open pool area—for residents in the second group who enter the pool area during open pool hours.

However, the computer system can define a resident group in any other way and a group access perimeter for these residents according to any other variable or parameter in Blocks S120 and S122.

7. Individual Access Perimeter

Block S130 of the method S100 recites defining a first individual access perimeter excluding a first portion of the generic access. (Block S130 can similarly recite removing a section of the access perimeter assigned to a first resident, in the set of residents, to define an individual access perimeter for the first resident.) Generally, in Block S130, the computer system adjusts a generic access perimeter (or a group access perimeter) for a particular resident—such as by extending or retracting the boundary of the generic access perimeter—to define an individual access perimeter tailored to unique needs or risks of the particular resident. In particular, the computer system can define an individual access perimeter—specific to one resident—that differs from the generic access perimeter in order to permit this resident to access more areas of the facility than other residents and/or to restrict this resident from areas of the facility that are accessible to other residents, as shown in FIGS. 4A-4C.

In one implementation, the computer system cooperates with an administrator to define individual access perimeters for select residents of the facility. In particular, the computer system can: assign a large, generic access perimeter around the facility to all residents in Block S112; and assign smaller access perimeters within particular regions of the facility to select residents in Block S130, such as based on each resident's mobility status, mental health, memory status, and/or perimeter breach event history, etc.

In one example, for a resident exhibiting memory loss, the computer system can define an individual access perimeter inset from the generic access perimeter, such as by a fixed distance or by a distance proportional to a degree of memory loss exhibited by the resident and/or by a distance proportional to a degree of cooperation the resident exhibits toward care providers in the facility.

In another example, for a particular resident exhibiting low mobility, the computer system can remove all floors of the facility except the floor containing the particular's resident's personal room and/or remove all stairwells from the generic access perimeter to define an individual access perimeter for the particular resident. In yet another example, the generic access perimeter can exclude residents' private rooms; for a particular resident, the computer system can add a private room—assigned to the particular resident's—to the generic access perimeter in order to generate an individual access perimeter unique to the particular resident; the computer system can repeat this process for each other resident of the facility.

In a similar example, the computer system can: access a characteristic of a resident, such as from a resident profile or health record associated with the resident; incorporate a public common space within the facility into an individual access perimeter for this resident; and exclude a second space—inside or around the facility—from the resident's individual access perimeter based on a predefined rule for supervision of residents exhibiting this characteristic when occupying the second space. Based on this individual access perimeter, the computer system can then serve prompts to care provider mobile devices in the facility to assist or supervise the resident when the location of resident's wearable device indicates that the resident is approaching or has entered the second space.

Similarly, the generic access perimeter can exclude laundry, kitchen, and office areas within the facility; for a particular resident provided laundry and kitchen privileges or employed by the facility to aid with administrative tasks, the computer system can add these spaces to the generic access perimeter to define an individual access perimeter for the particular resident.

The computer system can therefore (uniquely) modify the generic access perimeter for a resident to define an individual access perimeter specific to this resident in Block S130, regularly check that the resident is located within her assigned access perimeter, and then trigger an alarm to retrieve or serve the resident in Block S150 if her assigned wearable device is determined to be outside of her assigned access perimeter. However, the computer system can construct an individual access perimeter in any other way and based on any other parameters or characteristics of the corresponding resident.

8. Dynamic Individual Access Perimeter

The computer system can also dynamically adjust an individual access perimeter for a resident over time based on various factors, such as: time of day; locations of care providers nearby; locations of other residents within the facility; and/or scheduled events and visits, etc., as shown in FIGS. 4A-4C.

8.1 Time

In one implementation shown in FIG. 4A, the computer system adjusts an individual access perimeter for a resident based on a daily schedule. For example, the computer system can: restrict the resident's individual access perimeter to the resident's assigned room, a nearest bathroom, and a hallway therebetween during night hours (e.g., from 11 PM to 5 AM); expand the resident's individual access perimeter to include an interior sitting area and interior dining area during breakfast hours (e.g., from 5 AM until 9 AM); expand the resident's individual access perimeter to its maximum area (e.g., the generic access perimeter) during visiting hours (e.g., from 9 AM until 6 PM); reduce the resident's individual access perimeter to interior and exterior sitting areas, dining areas, and game rooms during extended dinner hours (e.g., from 6 PM until 7 PM); remove dining areas from the resident's individual access perimeter during evening hours (e.g., from 7 PM until 11 PM); and repeat this cycle for the next day. In this example, the computer system can adjust the resident's individual access perimeter according to preset weekday and weekend schedules, such as generic daily schedules applicable to all residents of the facility. Alternatively, the computer system can adjust the resident's individual access perimeter based on daily schedules specific to the resident (or to a group of residents) and defining more specific waking, eating, exercising, and socializing periods for the resident.

In a similar example, the system: assigns the generic access perimeter to a first resident during a daytime period; defines a first individual access perimeter spanning a first private room assigned to the first resident, containing interior public spaces within the facility, and excluding private rooms assigned to other residents in the facility; and then assigns the first individual access perimeter to the first resident during a nighttime period. The computer system can similarly define individual access perimeters for other residents in the facility and thus transition from activating a generic access perimeter across a population of residents in the facility during daytime hours to activating a unique, individual access perimeter for each resident during nighttime hours.

8.2 Care Provider Location

Figure 7:
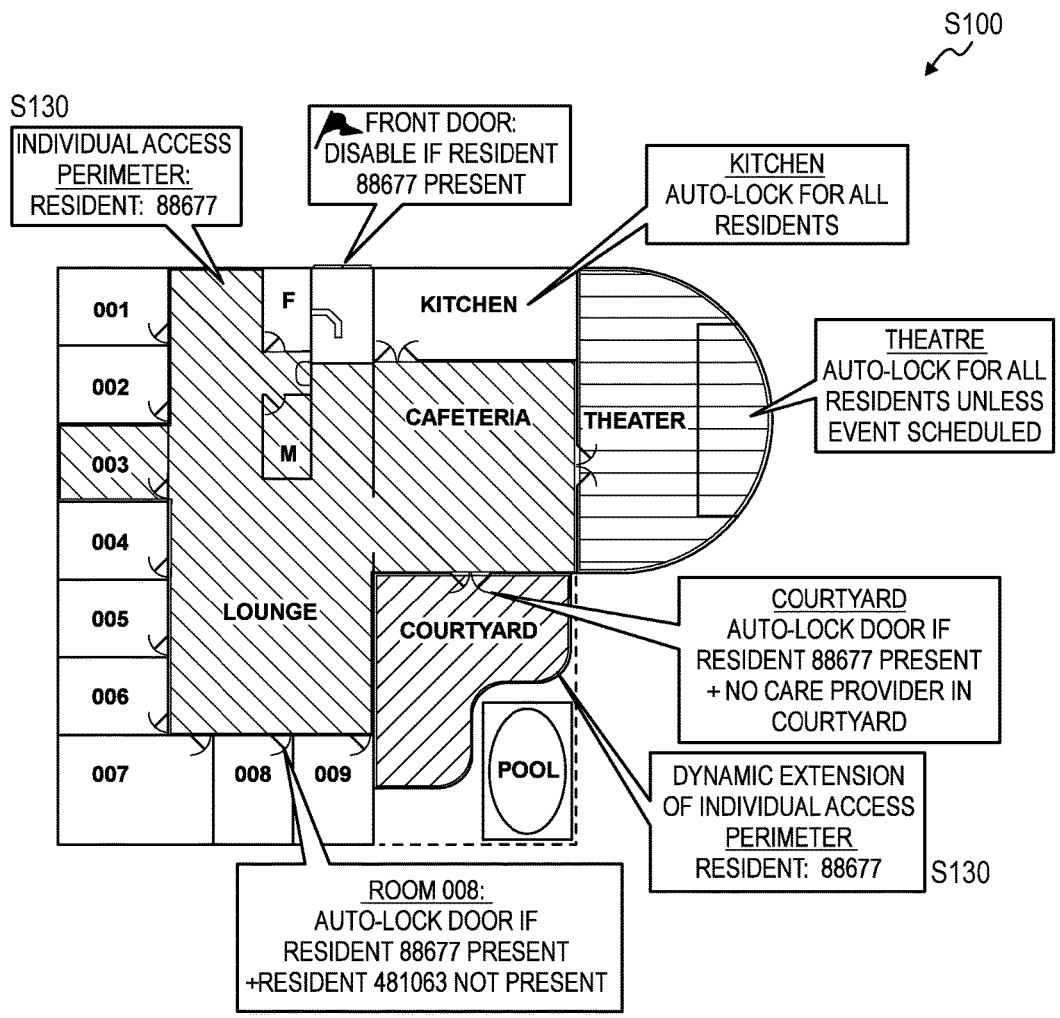
FIG. 7 is a schematic representation of one variation of the method.

In another implementation shown in FIG. 7, the computer system adjusts a resident's individual access perimeter based on the resident's proximity to a care provider. For example, the computer system can: retrieve a preset maximum distance between the resident and a nearest care provider; retrieve a current location of each care provider within the facility, such as based on locations of mobile or wearable devices assigned to each care provider; populate a virtual care provider access map with circular areas, each centered on the current location of one care provider and of radius equal to the preset maximum distance; calculate the intersection of the virtual care provider access map and the current maximum access perimeter assigned to the resident; and store this intersection as the resident's current individual access perimeter.

In the foregoing example, the computer system can calculate the maximum distance between the resident and a care provider based on various parameters. For example, the computer system can reduce the maximum distance (e.g., from a generic maximum distance) if the resident: has exhibited a tendency to intentionally or unintentionally breach her assigned access perimeter in the past; suffers from memory loss; has been involved in oral or physical altercations with other residents in the past; is currently not accompanied by another resident or scheduled visitor; or is obscured from a care provider's view by too many other residents nearby. Similarly, the computer system can increase the maximum distance (e.g., from a generic maximum distance) if the resident: is accompanied by several other residents or by a scheduled visitor; is occupying her private room; or has little or no history of intentional or unintentional perimeter breaches. The computer system can also decrease the minimum distance if fewer care providers than scheduled are currently on duty within the facility or available to assist the resident, such as if certain care providers are busy assisting another resident who has fallen or breached his assigned access perimeter.

Furthermore, once locations of care providers throughout the facility are determined, the computer system can: filter this set of care providers to those within eyeshot of the resident, such as by comparing resident and care provider locations to known locations of walls and windows in the facility (e.g., as defined in the vectorized map of the facility described above); populate the virtual care provider access map with circular areas representing positions of these care providers currently within view of the resident; and calculate an individual access perimeter accordingly.

Similarly, in this implementation, the computer system can expand the resident's access perimeter—beyond a preset maximum access perimeter—if a care provider is near the resident. For example, the computer system can: retrieve a current location of each care provider within the facility; populate a virtual care provider access map with circular areas, each centered on the current location of one care provider and of radius equal to the generic or resident-specific maximum distance; calculate the union of the virtual care provider access map and the current maximum access perimeter assigned to the resident; and store this union as the resident's current individual access perimeter. Therefore, the computer system can enable a care provider to freely escort the resident throughout the facility without triggering a perimeter breach event, despite the maximum access perimeter currently assigned to the resident. The computer system can implement similar methods and techniques to incorporate access to an exercise facility, public indoor space, and/or public outdoor space, etc.—automatically and in real-time—when care providers enter and occupy these spaces.

Therefore, in this implementation, the computer system can: track locations of a first care provider mobile device associated with a first care providers active within the facility over a period of time; define a first care provider response area containing and extending outwardly from locations of the first care provider mobile device over the period of time; and extending a first individual access—assigned to a first resident—to incorporate the first care provider response area during this period of time.

The computer system can repeat the foregoing process(es) to calculate a new individual access perimeter for the resident upon receipt of new locations of the resident and care providers, thereby dynamically adjusting the resident's individual access perimeter over time.

The computer system can implement similar methods and techniques to update a generic access perimeter and/or group access perimeters in (near) real-time based on locations of care providers throughout the facility.

8.3. Interpersonal Conflict

The computer system can similarly adjust the resident's individual access perimeter based on locations of other residents nearby. In one implementation shown in FIG. 4C, the computer system defines non-intersecting (and offset) access perimeters for two residents who have previously experienced interpersonal conflict, such as oral arguments or physical altercations. For example, the computer system can extract indicators of interpersonal conflict between a first resident and a second resident from electronic incident reports previously entered by care providers at the facility or from complaints previously submitted by residents of the facility. In another example, the computer system can predict interpersonal conflict between the first and second resident based on historical resident location and activity data. In this example, for the first resident who has experienced multiple falls in the past, the computer system can: scan resident location data for locations of other residents near (e.g., within two meters of) the first resident's location during each fall event; identify a second resident who was near the first resident during each or most of the first resident's previous fall events; predict that the second resident was responsible for the first resident's falls accordingly; and predict interpersonal conflict between the first and second resident accordingly. However, the computer system can implement any other methods or techniques to predict interpersonal conflict between the first and second residents based on past incident data collected at the facility.

The computer system can then define non-intersecting access perimeters for the first and second residents to preempt future altercations between the first and second residents as a result of their proximity. In particular, the computer system can: track locations of a second resident wearable device—associated with a second resident— within the facility over a period of time; and regularly update a first individual access perimeter assigned to a first resident (e.g., on a five-second interval) to exclude restriction zones containing locations of the second resident wearable device over the period of time responsive to the second resident being flagged for separation from the first resident. For example, the computer system can select a minimum distance between the first and second residents, such as: a static minimum distance of five meters; or a minimum distance of ten meters if interpersonal conflict between the first and second residents has historically included physical violence and five meters if such interpersonal conflict has historically resulted in oral altercations only. (The computer system can simultaneously implement similar methods to modify a second individual access perimeter assigned to the second resident based on locations of the first wearable device assigned to the first resident.)

The computer system can also adjust the minimum distance based on the location occupied by the first and second residents. For example, when the first and second residents are occupying a busy dining area or when the first and second residents are occupying a smaller, crowded theatre, such as for entertainment hosted at the facility, the computer system can decrease the minimum distance (e.g., by 50%) to allow the first and second residents to find seats within the cafeteria or theatre without triggering a perimeter breach event. In another example, when the first resident is occupying a first room and the second resident is passing through the first room on her way to another room in the facility, the computer system can reduce the minimum distance to enable the second resident to pass through the first room without triggering a perimeter breach event, such as only if at least one care provider or at least five residents are occupying the first room near the first resident. However, when the first resident is occupying a space within the facility alone or with only a few other residents (e.g., a bathroom), the computer system can increase the minimum distance (e.g., by 50%) when the second resident approaches the first resident's location. In yet another example, when a care provider is within five meters of either the first or second resident, the computer system can disable the minimum distance requirement for the first and second residents. However, the computer system can adjust the minimum distance between the first and second residents according to any other parameter or context of a space occupied by the first and second residents.

The computer system can then adjust individual access perimeters assigned to the first and second residents according to this minimum distance. In one example, if the first resident is currently occupying a first location (partially or fully) inside of a second access perimeter assigned to the second resident and the second resident is currently occupying a second location (partially or fully) inside of a first access perimeter assigned to the first resident, the computer system can: define a first circular restriction zone centered on the first resident's location and of a radius equal to the minimum distance; subtract the first circular restriction zone from the second access perimeter assigned to the second resident; define a second circular restriction zone centered on the second resident's location and of a radius equal to the minimum distance; and subtract the second circular restriction zone from the first access perimeter assigned to the first resident. In a similar example, the computer system can: track locations of both resident wearable devices and care provider mobile devices within the facility; define a restriction zone centered on a second location of a second resident wearable device and of a radius proportional to a distance from the second location to a nearest care provider mobile device responsive to the second resident being flagged for separation from the first resident (e.g., in a resident management file or in the first resident's personal file at the facility); remove the restriction zone from a first individual access perimeter assigned to the first resident; and repeat this process as the first resident, the second resident, and care providers move throughout the facility over time (e.g., once per five-second interval).

In this implementation, the computer system can update the first and second circular restriction zones and the first and second access perimeters substantially in real-time (e.g., once per minute or once per five-minute interval) as the first and second residents move toward and away from each other over time in Block S130. The computer system can then trigger an alarm if motion of the first resident moves into the second resident's individual access perimeter or vice versa.

In this implementation, in response to a first location of the first resident wearable device falling beyond a perimeter of the first individual access perimeter assigned to the first resident at a first time, the computer system can distribute a first breach event prompt—to retrieve the first resident from proximal the first location—to care provider mobile devices near the first location. However, in response to a second location of the first resident wearable device falling within a restriction zone defined in the first individual access perimeter at a second time, the computer system can distribute a second breach event prompt—to maintain separation between the first resident and the second resident proximal the second location—to care provider mobile devices near the second location. The computer system can therefore indicate a type of a breach event involving a resident—such as a boundary-type breach event or conflict-based breach event—in a breach event prompt transmitted to care provider mobile devices in Block S150 responsive to detecting such a breach event involving the first resident.

8.4 Group Location

The computer system can implement similar methods and techniques to bound the location of two residents in close proximity, such as: two residents known to provide emotional support to one another; a group of residents who are scheduled for the same current or upcoming activities; or a group of residents who have historically remained in close proximity at similar times on similar days in the past.

In one implementation, the computer system can implement methods and techniques described above to track the locations of residents within the facility over time. For a particular resident, the computer system can identify a group of other residents who have consistently occupied spaces near and around the particular resident (e.g., within ten meters of the particular resident) at similar times on similar days (e.g., the past twenty weekdays or the past ten Tuesdays for the current day that is a Tuesday). The computer system can then: retrieve last locations of these other residents; identify a cluster of these locations representative of the group (e.g., containing at least 80% of the last locations of the filtered set of residents and excluding location outliers); and define a smooth boundary encompassing this cluster of locations. The computer system can then define an individual access perimeter that contains this smooth boundary (and a nearest bathroom and a path therebetween) and assign this individual access perimeter to the particular resident. (The computer system can similarly assign the individual access perimeter to each other resident in the group.)

The computer system can repeat this process over time, such as following receipt of new location data for each resident in the group, to update this group-dependent access perimeter for the particular resident in Block S130. Thus, when the particular resident—who commonly moves throughout the facility with other residents in this group or commonly occupies spaces within the facility with other residents in this group—moves beyond this group-dependent access perimeter, such as by actively moving away from the group or by remaining in a space while the group moves away, the computer system can label such behavior as anomalous and trigger an alarm prompting a care provider to check in on the particular resident in Block S150. For example, the computer system can: prompt a care provider to visit the particular resident's location immediately if the resident is alone; or delay triggering a perimeter breach alarm, such as for two minutes, if another resident is detected near (e.g., within two meters of) the particular resident at the time of this perimeter breach event.

8.5 Visitors and Scheduled Events

The computer system can also modify an individual access perimeter for a resident while the resident is seen by a visitor at the facility, such as a friend, family member, doctor, or other guardian, as shown in FIG. 4B.

In one implementation, the computer system can expand the resident's individual access perimeter to the full extent of the facility or campus (e.g., to the full extent of the generic global boundary)—less private and restricted areas (e.g., residents' rooms, closed exercise facilities, etc.)—thereby enabling the resident to walk throughout the facility with her visitor without triggering a perimeter breach event. In this implementation, the computer system can also expand the resident's individual access perimeter, such as by ten meters beyond the generic access perimeter or up to the perimeter of the campus, to enable the resident and the visitor to complete a longer walk together or to find a more private setting on the campus. The computer system can also incorporate private or otherwise restricted areas of the facility into the resident's individual access perimeter, such as a private meeting room (e.g., for the visitor who is an attorney or accountant), a private examination room (e.g., for the visitor who is a doctor), an on-site salon (e.g., for the visitor who is a barber or hair stylist), or an exercise room (e.g., for the visitor who is a physical therapist).

In this implementation, the computer system can also extend the resident's individual access perimeter—just prior to her visitor's scheduled arrival and until her visitor's scheduled departure—to include the main entrance of the facility, a visitor parking lot near the facility, and/or a walkway therebetween, thereby enabling the resident to greet her visitor upon arrival and to walk her visitor to his car upon departure, and then returning to the facility without triggering a perimeter breach event.

Additionally or alternatively, the computer system can remove areas of the facility from the resident's individual access perimeter as the time of a scheduled visit nears—such as to include the entrance of the facility or a waiting room when the resident is scheduled to meet her visitor—to ensure that the resident is prepared to greet her visitor upon arrival.

Therefore, the computer system can: define a second individual access perimeter extending beyond an area spanned by the generic access perimeter; and assign the second individual access perimeter to the first resident during a limited period of time while a visitor of the first resident is present in the facility. (In this implementation, the computer system can also interface with wireless hubs throughout the facility to track a temporary access pass issued to the visitor and activate the second individual access perimeter for the first resident while the access pass is within a threshold distance (e.g., five meters) of the first resident's wearable device and then revert back to the first individual access perimeter for the first resident when the access pass is deactivated or detected outside of this threshold distance from the first resident's wearable device.)

The computer system can implement similar methods and techniques to extend and retract the resident's individual access perimeter based on other events scheduled in the facility. For example, in preparation for and during a scheduled meeting between the first resident and a care provider in a restricted area in the facility (e.g., an administrator office), the computer system can automatically extend the first resident's access perimeter to include this restricted area In another example, just before, during, and immediately after a play, movie screening, or other theatrical event scheduled in a theatre or auditorium in the facility, the computer system can extend generic, group, and individual access perimeters for residents in the facility to include the theatre or auditorium, such as for all residents of the facility or for residents who previously confirmed attendance at the theatrical event, as shown in FIG. 4B.

8.6 Resident Characteristics

The computer system can also adjust the individual access perimeter for the resident according to various resident-dependent parameters. For example, the computer system can maintain access to the resident's private room in all individual access perimeters for the resident at all times unless the resident has a history of depression, self-harm, or insufficient activity level. In this example, the computer system can: remove the resident's private room from her individual access perimeter over periods of time during which the resident should be active or engaging with other residents in the facility, such as between 10 AM and 2 PM and between 5 P and 7 PM on weekdays; and only incorporate the resident's room in her individual access perimeter outside of these time windows if the resident has a history of depression, low community engagement or interest, and/or low activity levels. Similarly, the computer system can maintain a nearest two bathrooms and paths to the nearest two bathrooms in all individual access perimeters for the resident at all times, unless the resident has a history of hiding in bathrooms.

Similar to the example described above, the computer system can maintain a list of residents who are able to swim. If the resident is included in this list, the computer system can extend the resident's individual access perimeter to include a pool area during recreation hours or during pool hours at the facility. However, if the resident is not included in this list, the computer system can extend the resident's individual access perimeter up to a threshold distance from the pool—such up to five meters from the edge of the pool—but not the pool itself during recreation hours or during pool hours. In this latter case, the computer system can extend the resident's individual access perimeter to include the pool if a care provider is determined to be occupying the pool or is within two meters of the resident while the resident is present in the pool.

Similarly, the computer system can maintain a list of residents prescribed inactivity or low activity; if the resident is included on this list, the computer system can remove exercise facilities from the resident's individual access perimeter unless accompanied by any care provider or specifically by a physical therapist.

8.7 Resident History

In another implementation, the computer system can track the resident's location over time—such as over multiple days, weeks, months, or years—and extract trends from these location data to predict the resident's location at the current time and/or at future times. For example, the computer system can identify trends in the resident's location at similar times on similar days in the past and then transform these trends into a dynamic time-dependent individual access perimeter for the resident that encompasses the resident's predicted location at any given time. In this example, the computer system can: calculate a confidence score for the predicted location of the resident at the current time based on clustering density of past resident locations at similar times on similar days in the past (e.g., same days of the week, past days within the same month or quarter, past sunny days, past cold days, past weekdays, past weekend days, etc.); define a predicted location area—for each specific instance in time—of radius inversely proportional to a corresponding confidence score; and center the predicted location area at the centroid of this set of past resident locations. The computer system can then define the resident's current individual access perimeter that encompasses the predicted location area. The computer system can repeat this process over time to update the size and location of the predicted location area—and therefore the resident's individual access perimeter—based on past locations of the resident at similar times. Therefore, if the resident's current location falls outside of the current individual access perimeter calculated for the resident, the computer system can label the resident's current location as anomalous and dispatch a care provider to check in on the resident in Block S150.

In a similar example, the computer system can: average past locations of the resident at similar times on similar past days; remove outliers from this set of locations; define an individual access perimeter containing the remaining locations; and assign this individual access perimeter to the resident in Block S130. However, the computer system can implement any other method or technique to define an individual access perimeter for the resident based on historical trends in the resident's location.

8.8 Risk

In another implementation, the computer system can: calculate a perimeter breach event risk for the resident based on a frequency of past perimeter breach events involving the resident; and then curtail the resident's individual access perimeter proportional to the resident's perimeter breach event risk or if the resident's perimeter breach event risk exceeds a risk threshold. For example, for the resident who has triggered three perimeter breach events within the span of a single week, the computer system can assign to the resident an individual access perimeter offset inside the generic access perimeter by ten meters in Block S130; the computer system can thus detect and respond to a possible perimeter breach event involving the resident in Block S150 significantly before the resident reaches the generic access perimeter assigned to other residents of the facility and before the resident moves beyond a range of wireless communication hubs interspersed throughout the facility, at which point the resident may no longer be traceable through her wearable device. In this implementation, when serving prompts to care providers to respond to a perimeter breach event by the resident, the computer system can: initially serve a low-alert visual prompt to observe the resident when the resident first crosses her assigned individual access perimeter; serve a moderate-alarm prompt to move toward the resident's current location once the resident is within five meters of the generic access perimeter assigned to other residents of the facility; and then serve a high-alert prompt to care providers on duty to retrieve the resident once the resident moves beyond the generic access perimeter in Block S150, as described below.

In a similar example, the computer system can assign the generic access perimeter to a first resident by default. Responsive to subsequent breach events from this generic access perimeter by the first resident at a particular location within the facility, the computer system can: define a first individual access perimeter that excludes a portion of the generic access perimeter containing the particular location; and assign this individual access perimeter to the resident accordingly.

8.9 Dynamic Generic and Group Access Perimeters

The computer system can implement similar methods and techniques to automatically modify a generic access perimeter assigned to residents in the facility by default and/or to modify a group access perimeter assigned to a subset of residents in the facility based on events at the facility, characteristics of these residents, etc.

For example, the computer system can implement methods and techniques described above to update a generic access perimeter, group access perimeters, and individual access perimeters—assigned to residents of the facility—to selectively include and exclude public spaces within the facility based on a calendar of scheduled events in the facility, such as to selectively include: an exercise area during exercise hours or when a care provider is present in the exercise area; a theatre when a theatrical event is scheduled; or a cafeteria during scheduled meal times.

9. Perimeter Breach

Block S150 of the method S100 recites, in response to a second location of a second resident wearable device associated with a second resident, in the set of residents, falling outside of the generic access perimeter, assigned to the second resident, at a second time, distributing a second breach event prompt to assist the second resident proximal the second location to care provider mobile devices associated with care providers affiliated with the facility. Generally, in Block S150, the computer system notifies care providers within and around the facility that a resident has moved beyond her assigned (custom or generic) access perimeter substantially in real-time, shown in FIGS. 1 and 3, thereby enabling these care providers to rapidly attend to residents who are not where they should be while also allowing these care providers to personally engage with and assist other residents without perpetually focusing attention to whether another resident is or is not where she should be.

9.1 Resident Location Tracking

As described above, the computer system regularly tracks the resident's location in Block S140 and compares the resident's location to her assigned access perimeter in Block S150. In one implementation, the resident's wearable device broadcasts a test signal once per sampling period, receives response signals and UUIDs from local wireless communication hubs within the facility, and uploads these data to the computer system via a local wireless communication hub; the computer system then transforms these data into a location area or point of the resident's wearable device based on known geospatial positions of the wireless communication hubs recorded in a database or lookup table. The computer system can thus calculate a new location of the resident wearable device for each sampling period, compare this location to the access perimeter assigned to the resident, as described above, and trigger a perimeter breach alarm if the resident's location area overlaps the access perimeter or if the resident's location point has moved outside of (or is inside but within a threshold distance of) the assigned access perimeter.

Alternatively, the resident's wearable device can automatically retrieve its geospatial location, such as once per sampling period, and transmit this location to the computer system. The computer system can then compare this geospatial location to the resident's access perimeter and trigger a perimeter breach alarm if the geospatial location point is outside of—or is inside but within a threshold distance of—the assigned access perimeter.

9.2 Access Perimeter Approach

In one implementation, the computer system can determine that a resident is approaching her access perimeter and trigger a perimeter breach alarm or distribute a breach event prompt accordingly. For example, the computer system can determine an initial location of a resident wearable device based on wireless communications between the resident wearable device and a set of wireless communication hubs, as described above; and, in response to the initial location of the resident wearable device falling within a threshold distance of her access perimeter, distribute a perimeter observation prompt indicating the initial location of the resident and including a prompt to observe the resident. In one example shown in FIG. 3, in response to a resident moving to within ten feet of her assigned access perimeter, the computer system can distribute a prompt to a set of care provider mobile devices nearby in order to prompt these care providers: to move to locations within the facility at which the care providers can observe the resident; and to confirm that the resident is not attempting to breach the perimeter, such as without contacting the resident or otherwise engaging with the resident directly. The perimeter observation prompt can thus prompt care providers to visually observe (or "check on") a resident from afar as the resident nears her assigned access perimeter. In this example, the computer system can include the location of the resident in the prompt distributed to these care providers. The computer system can also include in this prompt a frequency of past perimeter breach events by the resident in order to indicate to these care providers a risk that the resident may breach her access perimeter or leave the facility.

In another implementation shown in FIG. 3, in response to the initial location of the resident falling within a threshold distance of her access perimeter, the computer system can identify care providers within a threshold distance of the resident, such as within 200 feet (or other threshold distance) of the resident or otherwise in a position to respond quickly to the resident's trajectory out of the facility, and distribute a perimeter observation prompt to a set of mobile devices associated only with care providers identified as located within a threshold distance of the resident. The computer system can also cross-reference locations of care provider mobile devices with a map of the facility at the time that the location of the resident falls within the threshold distance of her access perimeter and then determine which care provider mobile devices are within or almost within eyeshot of the resident (i.e., care providers with a direct visual path to the resident unobstructed by walls, floors, or other barriers) and distribute the perimeter observation prompt to these care provider mobile devices.

Therefore, in this implementation, in response to a first location of a first resident wearable device assigned to a first resident falling within a first individual access perimeter assigned to the first resident and in response to the first resident wearable device approaching a boundary of the first individual access perimeter at an initial time preceding the first time, the computer system can distribute a perimeter observation prompt to a care provider mobile device near this first location, wherein this perimeter observation prompt indicates the first location of the first resident and includes a prompt to observe the first resident. The computer system can later distribute a breach event prompt to the same care provider mobile device(s) within the facility in response to the first resident wearable device moving beyond the boundary of the first individual access perimeter, as described below.

9.3 Perimeter Breach Detection

In a similar implementation, the computer system can trigger a perimeter breach alarm only if the location of the resident is outside of or is inside but within a threshold distance of her access perimeter for a threshold period of time (hereinafter a "breach threshold time"). For example, the computer system can trigger a perimeter breach alarm in response to the location of the resident falling outside of her access perimeter for a period of time exceeding 60 seconds. In another example, an administrator of the facility may indicate through an administrator portal that it is customary at the administrator's facility to allow residents to greet incoming visitors and to walk outgoing visitors outside of the facility (e.g., at a front door). In this example, the computer system can trigger a perimeter breach alarm only after determining that the resident has been outside of her access perimeter for more than a breach threshold time, such as five minutes, accordingly.

The computer can also assign custom breach threshold times to each resident of the facility. For example, the care providers or managers at a facility may identify—within a care provider or manager portal hosted by the computer system—certain residents of the facility as "high-risk" for perimeter breach events, such as residents with Alzheimer's disease or residents with a propensity for violence. In this example, the computer system can automatically assign a null breach threshold time (i.e., a breach threshold time of zero seconds) to these high-risk residents while assigning other residents of the facility a breach threshold time of thirty seconds. In another example, the care providers or managers may identify residents of the facility with track records of good behavior ("low-risk" residents). The computer system can assign a breach threshold time of sixty seconds to these low-risk residents while assigning a null (or "0-second") breach threshold time to other residents. The computer system can therefore exhibit tolerance for low-risk residents occupying locations on the boundaries of their access perimeters while also rapidly issuing prompts to assist high-risk patients.

In another implementation, in order to compensate for possible error in localization of a resident based on communications between the resident's wearable device and hubs arranged throughout the facility, the computer system can: continue to calculate the location of the resident's wearable device over a sequence of scan periods following initial detection of the resident's wearable device outside of her assigned access perimeter; update a confidence score for a breach event involving this resident proportional to a duration or proportion of time that the resident's wearable device is subsequently determined to fall outside of the resident's access perimeter; and then transmit a breach event prompt to care provider mobile devices nearby once this confidence score exceeds a preset threshold, thereby limiting false positive breach events. In a similar example, once the computer system determines that the resident's wearable device has moved outside of the resident's assigned access perimeter at a first time, the computer system can: continue to track the location of the resident wearable device, such as at the same or increased frequency; record a continuous duration of time, from the first time, that the location of the first resident wearable device is located beyond the resident's access perimeter; and then distribute the first breach event prompt to care provider mobile devices nearby once this duration of time exceeds a preset threshold duration.

However, in Block S150, the computer system can function in any other way to detect and confirm a perimeter breach event.

9.4 Breach Event Prompt

In response to detecting and confirming a breach event in which a resident's wearable device is detected outside of her assigned access perimeter, the computer system can then distribute a breach event prompt to a set of care provider mobile devices—associated with care providers currently active in the facility—in (near) real-time in Block S150, as shown in FIGS. 1 and 3. Generally, in Block S150, the computer system can aggregate perimeter breach data—such as including the last known or current location of the resident, the resident's name, a photograph of the resident, and a mental health status (e.g., diagnosed degree of dementia), etc.—into a breach event prompt. The computer system can then transmit instances of the breach event prompt to mobile devices associated with all or a subset of care providers currently on duty within the facility. For example, in response to a perimeter breach event, the computer system can implement methods and techniques similar to those described above to filter all care providers currently on duty to a subset of care providers who specialize in oral communications with residents, who are associated with positive resident collection results, or who have developed a relationship with the resident who breached his access perimeter.

In response to a perimeter breach event, the computer system can also identify and elect additional recipients of the breach event prompt outside of the facility. For example, in response to a perimeter breach event by a resident, the computer system can retrieve from a database contact data for a list of preferred contacts associated with the resident, such as a phone number or email address for each of a spouse or child. In response to a perimeter breach event, the computer system can communicate with computing devices affiliated with a preferred contact associated with the resident to identify contacts nearby (e.g., within a threshold distance, such as within one-quarter mile or within a five-minute walk, of) the resident. In this example, the computer system can then selectively transmit instances of the breach event prompt to computing devices associated with such contacts who are within the threshold distance of the resident.

However, the computer system can implement any other methods or techniques to generate a breach event prompt and/or to transmit the breach event prompt to care providers within the facility.

9.5 Post-Perimeter Breach Event Tracking

The computer system, the resident's wearable device, and/or other local devices can continue to track the location of the resident's wearable device following detection of a perimeter breach event, such as at the same or increased frequency. The computer system can then transmit resident location updates to care provider mobile devices substantially in real-time—such as to all care providers in the facility or to a particular care provider who elected to respond to this breach event prompt—until a care provider reaches the resident.

9.6 Breach Event Response

As described in U.S. patent application Ser. No. 15/880, 070, the computer system can also: deescalate the breach event prompt at a second care provider mobile device—within the set of care provider mobile devices that received the breach event prompt—in response to receipt of confirmation of intent to respond to the breach event prompt from a first care provider mobile device, thereby indicating to a second care provider carrying the second care provider mobile device that the breach event has been or is being handled.

As described above, the computer system can continue to track locations of resident wearable devices and care provider mobile devices even after a breach event is detected. The computer system can then confirm that a particular care provider has responded to the breach event based on proximity of the particular care provider's mobile device to the resident's wearable device, such as determined through direct communications between these devices or by localizing these devices based on communications between these devices and hubs at known locations throughout the facility. Accordingly, the computer system can authorize edit permissions for an electronic incident report—for this breach event—by the particular care provider, exclusive of other care providers who did not respond to the breach event (e.g., whose assigned mobile device's were not detected in close proximity to the resident's wearable device), as shown in FIG. 1.

10. Resident Wearable Device Presence Confirmation

In one variation, a resident wearable device incorporates a suite of sensors, confirms its presence on a resident based on outputs of these sensors, and triggers the computer system to prompt a care provider to assist the resident if the wearable device determines that it is not currently present on the resident.

In one implementation, the resident wearable device includes a temperature sensor and a motion sensor (e.g., an accelerometer). During operation (e.g., once the wearable device is installed on a resident's wrist), the wearable device can: scan the position sensor for changes in position of the wearable device; scan the temperature sensor for temperatures of an adjacent surface; confirm presence of the wearable device on a resident responsive to frequent changes in position of the resident wearable device and if temperatures—read by the temperature sensor—fall within a threshold range; and detect removal of the first resident wearable device from the first resident responsive to infrequent changes in position of the wearable device (e.g., an acceleration peak indicative of removal of the wearable device followed by prolonged "stillness") and if temperatures—read by the temperature sensor—fall outside of the threshold range.

The resident wearable device can additionally or alternatively detect its removal from the resident. For example, the wearable device can: regularly sample an accelerometer in the wearable device; determine possible removal of the wearable device from the resident upon detecting a peak acceleration that exceeds a preset threshold acceleration followed by a period of stillness; and then confirm removal of the wearable device from the resident if a temperature detected by the temperature sensor drops below a threshold temperature during or following this period of stillness.

The wearable device can then regularly broadcast whether it has confirmed its presence on a resident (or has not detected its removal from the resident) to nearby wireless hubs in the facility, such as once per five-second interval. While the wearable device has determined its presence on a resident, the computer system can implement methods and techniques described above to track the location of the wearable device, store locations of the wearable device as locations of the resident, and selectively issue breach event prompts for this resident responsive to the location of the wearable device moving outside of the access perimeter assigned to the resident.

However, upon receipt of confirmation of removal of the wearable device from the resident (or failed confirmation that the wearable device is still present on the resident), the computer system can immediately transmit a prompt to nearby care provider mobile devices to assist the resident. In particular, by storing the location of the wearable device and associating these locations with the resident while presence of the resident wearable device on the first resident is confirmed (or not refuted) by the wearable device, the computer system can store a last known location of the resident. Therefore, in response to detection of removal of the wearable device from the resident, the computer system can issue a prompt to assist the first resident—proximal the last know location of the resident—to care provider mobile devices associated with care providers currently active within the facility.

11. Automated Access Restriction

Figure 6:
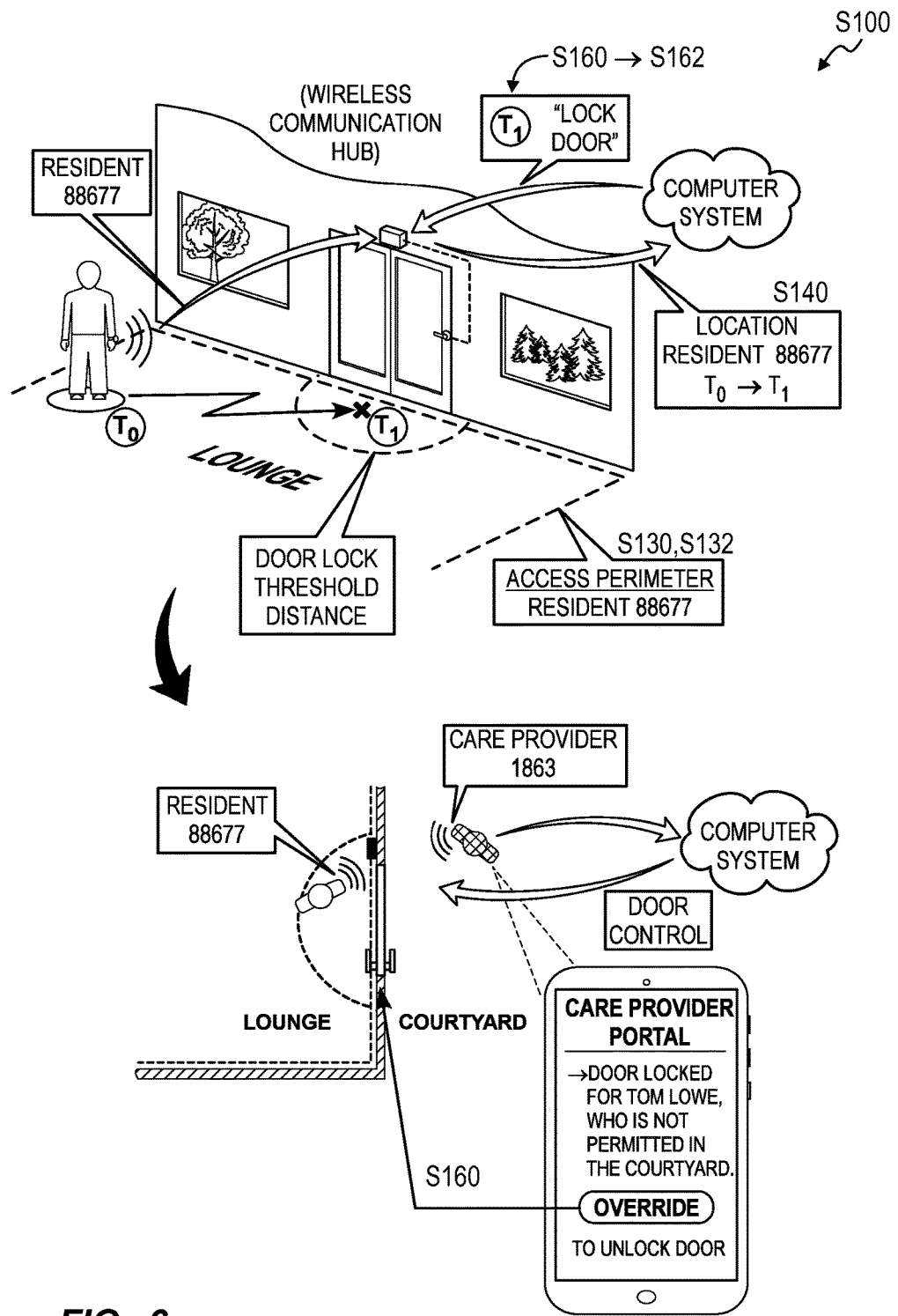
FIG. 6 is a flowchart representation of one variation of the method.

In one variation shown in FIGS. 5, 6, and 7, the method S100 includes: defining a generic access perimeter containing a first space and a second space separated by a door in Block S110; assigning the generic access perimeter to residents in a set of residents occupying the facility in Block S112; defining a first individual access perimeter containing the first space and excluding the second space in Block S130; assigning the first individual access perimeter to a first resident, in the set of residents in Block S132; maintaining the door in an unlocked state by default during a first period of time in Block S160; tracking locations of resident wearable devices associated with residents, in the set of residents, within the facility during the first period of time in Block S140; and, in response to a first location of a first resident wearable device associated with the first resident falling inside the individual access perimeter and within a threshold distance of the door during the first period of time, triggering the door to enter a locked state in Block S162.

In this variation, the method S100 can similarly include: defining an access perimeter containing a first space and excluding a second space within a facility, the first space and the second space separated by a door in Block S130; assigning the first individual access perimeter to a first resident, in a set of residents, occupying the facility in Block S132; maintaining the door in an unlocked state by default during a first period of time in Block S160; tracking locations of resident wearable devices associated with residents, in the set of residents, within the facility during the first period of time in Block S140; in response to a first location of a first resident wearable device associated with the first resident falling inside the individual access perimeter and within a threshold distance of the door at a first time during the first period of time, triggering the door to enter a locked state in Block S162; and, in response to the first resident wearable device moving outside of the threshold distance of the door at a second time succeeding the first time, triggering the door to return to the unlocked state in Block S160.

10.1 Applications

Generally, in this variation, the computer system can implement methods and techniques similar to those described above to assign an access perimeter to a resident in the facility and to track locations of this resident via a wearable device present (e.g., worn, carried) by the resident. In this variation, the computer system can further interface with a remotely-operable or remotely-lockable door in the facility to selectively disable or lock this door—located at a boundary of the resident's access perimeter—when the resident is detected near this door according to Blocks of this variation of the method S100. By thus remotely and selectively locking a door when a resident not permitted access through this door is present, the computer system can actively prevent this resident from moving beyond her assigned access perimeter without requiring care providers in the facility to actively monitor or retrieve this resident and without requiring this door to regularly remain locked, which may negative access by care providers, other residents, administrators, visitors, etc. moving throughout the facility. Therefore, the computer system can execute Blocks in this variation of the method S100: to maintain doors in the facility in unlocked states by default, which may improve transparency, trust, comfort, and convenience for care providers, residents, administrators, visitors, etc. occupying the facility over time; and to selectively lock doors in the facility responsive to presence of certain residents not permitted access through these doors.

For example, interior and/or exterior doors of the facility can be fitted with electromagnetic or electromechanical locks that can be actuated remotely by the system, such as via a local ad hoc network; the facility can additionally or alternatively include automatic doors that can be selectively disabled remotely, such as via a local area network. In this example, the computer system can maintain doors between public common spaces throughout the facility in an unlocked state by default in order to permit care providers, administrators, visitors, grounds crew, maintenance staff, and/or inspectors, etc. to move throughout the facility unimpeded by locked doors regardless of whether these entities have access to keys, badges, or access passes for these doors. The computer system can also track residents in the facility through their issued wearable devices, as described above, and then selectively trigger a door to lock (or selectively disable automatic operation of the door) as a first resident approaches the door—and before the first resident reaches the door—if the access perimeter assigned to this first resident excludes an interior or exterior space on the other side of this door, thereby automatically controlling the first resident's access throughout the facility according to the access perimeter assigned to this first resident. However, if a second resident's access perimeter extends beyond this door and the first resident is not within a threshold distance of the door, the computer system can maintain this door in the unlocked state as the second resident approaches and then passes through the door.

Furthermore, in this variation, a resident's wearable device can regularly confirm that it is still present on its assigned resident (or confirm that removal has not been detected) based on sensor data read from sensors integrated into the wearable device, such as a temperature sensor and a motion sensor, as described above. Therefore, as long as the wearable device confirms its presence on a resident (or fails to detect removal from the resident), the computer system can selectively trigger doors throughout the facility to lock when the resident's wearable device approaches doors separating areas of the facility authorized for the resident from areas of the facility not authorized for the resident. However, in the event that the resident removes the wearable device (or in the event that the wearable device is at a low battery state of charge), the wearable device can communicate these events to the system, and the computer system can serve a prompt to care providers in the facility in (near) real-time to assist the resident at the last known location of the resident's wearable device, such as described above.

According to this variation of the method S100, the computer system can also selectively disable an automatic trigger to lock a door at the boundary of an access perimeter assigned to a resident when the resident approaches this door, such as: when a care provider is present near the other side of the door; when a care provider is moving with (e.g., supervising) the resident as this resident approaches and moves through the door; when a visitor carrying an access pass is moving with (e.g., supervising) the resident as this resident approaches and moves through the door; or during an emergency event (e.g., when a fire alarm is active) at the facility; etc.

10.2 Door Types

In this variation, the computer system can interface with: an exterior door to unbounded exterior space; a door to an interior or exterior space exhibiting risk to a resident in the facility (e.g., an outdoor pool, an indoor exercise area, a kitchen); an interior door to a private space (e.g., a private bedroom, an administrator office); and/or an interior or exterior gate; etc. For example, these doors can include hinged doors with automatic locks, such as electromagnetic or electromechanical locks. In this example, the computer system can trigger a magnetic lock integrated into a door to activate in Block S162 and trigger this magnetic lock to deactivate in Block S160. Alternatively, these doors can include automated sliding doors. In this example, the computer system can disable automatic operation of these doors in Block S162 and return these doors to normal automatic operation in Block S160.

Furthermore, in this variation, the computer system can interface with these doors though wired or wireless connections with these doors (or with remotely-controlled locks or control retrofitted onto these doors) in Blocks S162 and S160.

10.3 Door Lock Flags

In one implementation shown in FIG. 7, when defining an access perimeter in Block S130 (or in Block S110 or Block S120) as described above, the computer system can: reference a map of the facility annotated with locations of remotely-controlled doors; automatically identify a set of remotely-controllable doors beyond the access perimeter or within a threshold distance (e.g., two meters) of the boundary of the access perimeter; and flag each of these doors for selective locking when a resident—assigned this access perimeter—approaches.

For example, when defining a first individual access perimeter for a first resident, the computer system can: access a map representing interior spaces, exterior spaces, and doors within the facility; define the first individual access perimeter—spanning an interior space and excluding an exterior space—within the map, as described above; automatically identify a door between the interior space and the exterior space and proximal a boundary of the first individual access perimeter; and then set a flag to trigger the door to enter the lock state in the presence of any resident wearable device assigned to the first resident while the first individual access perimeter is current for the first resident in Block S130. The computer system can then trigger this door to enter the locked state in response to proximity of a first resident wearable device—currently assigned to the first resident—to the door while this flag is set for the first individual access perimeter. However, if a care provider or visitor is supervising the first resident, an emergency alarm is active at the facility, etc., the computer system can selectively disable this flag for the door in the first individual access perimeter and thus enable the first resident to pass through the unlocked door.

Furthermore, in this example, when defining a second individual access perimeter for a second resident, the computer system can similarly: access this map; define the second individual access perimeter—spanning both the interior space and the exterior space—within the map; and disable or omit a flag to trigger the door to enter the lock state in the presence of the second resident accordingly in Block S130. Unless the first resident is approaching or within a threshold distance of the door, the computer system can thus maintain the door in the unlocked state when the second resident approaches the door.

In a similar example, the computer system can: identify a first resident as diagnosed with dementia based on an electronic health record of the first resident; exclude an exercise space within the facility from a first individual access perimeter assigned to the first resident based on a predefined rule for supervision of residents exhibiting dementia when occupying the exercise space; and then set a flag to trigger a door into the exercise space to enter the lock state in the presence of the first resident if no care provider mobile device is present in the exercise space in Block S130. In this example, the computer system can then: regularly track locations of care provider mobile devices and resident wearable devices throughout the facility in Block S140; maintain the door into the exercise space in an unlocked state by default during an open exercise period in the exercise space (e.g., every morning from 6 AM to 10 AM and from 3 PM to 7 PM); trigger the door to enter the locked state in response to a first resident wearable device assigned to the first resident falling within the threshold distance of the door during this open exercise period while the exercise space is vacant of care provider mobile devices; maintain the door into the exercise space in an unlocked state and send a prompt to observe the resident to a care provider mobile device occupying the exercise space during the open exercise period as the resident's wearable device approaches and passes through the door into the exercise space; and return the door into the exercise space to the locked state outside of this open exercise period.

In yet another example, the computer system can: define a first individual access perimeter that contains a public space within the facility and that excludes a second private room assigned to a second resident in the facility; and set a flag to trigger a door into the second private room to enter the lock state in the presence of the first resident while the first individual access perimeter is current for the first resident unless the second resident is present in the second private room. Thus, the computer system can trigger this door to enter the locked state in response to a first resident wearable device assigned to the first resident occupying the public space within a threshold distance of the second private room while a second resident wearable device associated with the second resident is absent from the second private room, thereby preventing the first resident from entering the second private room without supervision or oversight of the second resident.

10.4 Automatic Door Lock Trigger

Therefore, in this variation of the method S100, the computer system can maintain a door (or gate, etc.) in the facility in an unlocked state by default in order to permit care providers, administrators, visitors, grounds crew, maintenance staff, and/or inspectors, etc. to move through this access point substantially unimpeded, regardless of whether these entities have access to keys, badges, access passes, or other devices to positively confirm access through this access point. However, if a resident assigned an access perimeter that terminates inside of this door is approaching or occupying a location within a threshold distance of the door—such as determined by tracking a wearable device worn or carried by the resident—that system can automatically trigger the door to lock until the resident moves away from the door, thereby preventing this resident from passing through this door.

In one implementation, the computer system implements a preset threshold distance between the resident and the door to trigger the door to enter the locked state. For example, the computer system can implement a threshold distance (slightly) greater than a locational tolerance of wearable devices and/or wireless communication hubs throughout the facility to resolve locations of these wearable devices. In this example, for a locational tolerance of one meter for wearable devices and wireless communication hubs in the facility, the computer system can implement a threshold distance of two meters.

In another implementation, the computer system can: track motion of the resident's wearable device over time; calculate a speed of the resident over a period of time as the resident's wearable device approaches the door; and then set the threshold distance proportional to the speed of the resident, thereby preventing opportunity for the resident to run toward and open the door prior to the computer system triggering the door to unlock.

Alternatively, the computer system can interface with a care provider or administrator of the facility to set custom threshold distances for doors throughout the facility and/or for the resident. Similarly, the computer system can interface with a care provider or administrator of the facility to define other triggers for locking a door in the presence of a resident whose access perimeter terminates inside this door. However, the computer system can implement any other schema to trigger a door to enter the locked state responsive to proximity of a resident and the resident's assigned access perimeter.

10.5 Automatic Door Unlock Trigger

As described above, after locking a door responsive to proximity of a resident, the computer system can trigger the door to unlock in Block S160 once a risk or threat of the resident passing through the door decreases.

In one example, the computer system can trigger the door to lock when the resident's wearable device falls within a preset threshold distance of the door and then trigger the door to unlock once the resident's wearable device falls outside of this preset threshold distance of the door. In a similar example shown in FIG. 5, the computer system can implement hysteresis to: trigger the door to lock when the resident's wearable device falls within a first threshold distance of the door; and then trigger the door to unlock once the resident's wearable device falls outside of a second threshold distance—greater than the first threshold distance—of the door, therefore maintaining the door in the locked state until the resident has actively and intentionally moved away from the door.

10.6 Tracking and Door Proximity Confirmation

As described above, the computer system can track residents moving throughout the facility based on wireless communications between resident wearable devices assigned to these residents and wireless communication hubs distributed throughout the facility. The computer system can then selectively trigger a door to lock responsive to a wearable device assigned to a resident—not permitted to pass through this door—falling within a threshold distance of this door, as determined from wireless communications between this wearable device and wireless communication hubs near the door.

In this variation, remotely-controllable doors in the facility can also include wireless communication modules configured to detect resident wearable devices nearby; and the computer system can confirm proximity of a resident to a door based on wireless communications between the wireless communication module in (or adjacent) the door and the resident's wearable device. For example, the computer system can: track locations of a resident wearable device based on wireless communications between the resident's wearable device and a set of wireless communication hubs distributed throughout the facility in Block S140; confirm proximity of the resident's wearable device to the door based on wireless communications between the resident's wearable device and a wireless unit arranged on or near the door in Block S140; and then trigger the door to enter the locked state in response to communications between the resident's wearable device and the wireless unit confirming proximity of the resident's wearable device to the door.

10.7 Automatic Door Lock Disablement

In this variation, the computer system can also selectively disable a flag to lock a door when a resident—assigned an access perimeter bounded inside the door—approaches and/or returns the door from the locked state to the unlocked state even in the presence of the resident responsive to commands from care providers, responsive to presence of care providers or visitors, or responsive to alarm conditions at the facility.

In one example, when a resident assigned an access perimeter that terminates inside of a door approaches this door, the computer system can automatically trigger the door to lock. However, if the computer system then detects a care provider mobile device approaching the opposite side of the door, the computer system can trigger the door to return to the unlocked state, thereby permitting the care provider to pass through the door. In this example, the computer system can also transmit a notification to the care provider's mobile device—in (near) real-time—indicating that the resident nearby is not permitted past the door, such as by sending a name and/or a photographic image of the resident to the care provider's mobile device and an alert to confine the resident.

In a similar example, when the resident is approaching a door located just outside of her assigned access perimeter but a care provider mobile device is detected on the opposite side of the door and within a threshold supervising distance of the door, the computer system can maintain the door in the unlocked state, thereby enabling the resident to interact directly with the care provider rather than through a locked door. As in the foregoing example, the computer system can also transmit a notification to the care provider's mobile device to indicate that the resident nearby is not permitted (far) past the door.

The computer system can also provide manual control to care providers to unlock a door thus locked responsive to proximity of a resident not permitted to pass through this door. In one example shown in FIG. 6, after triggering a door to enter a locked state responsive to proximity of this resident, the computer system can transmit a notification to a care provider mobile device proximal the door (e.g., all care provider mobile devices within five meters of the door), wherein the notification: indicates that the computer system has transitioned the door into the locked state responsive to proximity of the first resident; and includes an option to return the door to the unlocked state. Thus, in response to selection of an override command at the care provider mobile device, the computer system can trigger the door to return to the unlocked state. In this example, the computer system can serve this notification to a mobile device (e.g., a smartphone, a smartwatch) carried or worn by the care provider; the mobile device can render this notification on a home screen, on a locked screen, or within a native application executing on the mobile device and can return a command to the computer system to unlock the door if the care provider selects or swipes this notification. The computer system can then trigger the door to unlock accordingly, thereby providing the care provider one-click or one-swipe override control for the locked door even when a resident is nearby who is not permitted to pass through this door.

In yet another example, the computer system can track locations of both resident wearable devices and care provider mobile devices throughout the facility and can determine that a particular care provider is supervising or escorting a resident based on proximity and concurrent motion of the particular care provider's mobile device and the resident's wearable device over a period of time. If the computer system thus derives such a link between the particular care provider's mobile device and the resident's wearable device, the computer system can automatically disable a flag to lock a door outside of the resident's access perimeter when the particular care provider's mobile device and the resident's wearable device approach and pass through this door.

The computer system can implement similar methods to track an active access pass—temporarily assigned to a visitor—moving through the facility, to link active access pass to a resident, and to disable a flag to lock a door outside of the resident's access perimeter when the access pass and the resident's wearable device approach and pass through this door. In particular, in response to the access pass and the resident's wearable device falling within a preset supervising distance and moving together toward the door, the computer system can maintain the door in the unlocked state as the access pass and the first resident wearable device approach and pass through the door. Alternatively, an administrator can manually link the access pass to the resident, and the computer system can automatically disable a flag to lock a door outside of the resident's access perimeter when the access perimeter and the resident's wearable device approach and pass through this door. Yet alternatively, when a visitor arrives at the facility to visit the resident, the computer system can temporarily modify the resident's access perimeter to enable the resident and the visitor to access spaces from which the resident restricted when not accompanied or supervised by the visitor.

In yet another example, when an alarm is active in the facility—such as a fire alarm—the computer system can disable a flag to lock a door—outside of the access perimeter of a resident—when the resident approaches the door in order to permit the resident to exit the facility.

However, the computer system can selectively unlock or selectively disable a flag to lock a door responsive to proximity of a resident based on any other event or command.

10.8 Lock Inversion

Alternatively, in this variation, the computer system can maintain doors throughout the facility in the locked state and then selectively unlock a door when: a care provider, administrator, visitor, grounds crew, maintenance staffer, and/or inspectors, etc. carrying an authorized care provider or an active access pass approaches the door; and when a resident assigned an access perimeter that extends beyond this door approaches the door. In this variation, the computer system can implement methods and techniques described above: to maintain a door in the locked state when other residents not permitted to pass through this door are present; and to selectively trigger the door to unlock responsive to commands from care providers, alarm conditions at the facility, etc.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a resident computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated within apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for controlling access within an assisted living facility comprising:
    defining a generic access perimeter containing a first space and a second space separated by a door;
    assigning the generic access perimeter to residents in a set of residents occupying the facility;
    defining a first individual access perimeter containing the first space and excluding the second space;
    assigning the first individual access perimeter to a first resident, in the set of residents;
    maintaining the door in an unlocked state by default during a first period of time;
    tracking locations of resident wearable devices associated with residents, in the set of residents, within the facility during the first period of time; and
    in response to a first location of a first resident wearable device associated with the first resident falling inside the individual access perimeter and within a threshold distance of the door during the first period of time, triggering the door to enter a locked state.

2. The method of claim 1, further comprising, triggering the door to return to the unlocked state in response to the first resident wearable device remaining inside the individual access perimeter and moving outside of the threshold distance from the door.

3. The method of claim 2, wherein triggering the door to return to the unlocked state comprises triggering the door to return to the unlocked state in response to the first resident wearable device moving outside of a second threshold distance, greater than the threshold distance, from the door.

4. The method of claim 2:
    wherein triggering the door to enter the locked state comprises triggering a magnetic lock integrated into the door to activate; and
    wherein triggering the door to return to the unlocked state comprises triggering the magnetic lock to deactivate.

5. The method of claim 1:
wherein defining the first individual access perimeter comprises:
accessing a map of the facility, the map representing interior spaces, exterior spaces, and doors within the facility;
defining the first individual access perimeter within the map, the first individual access perimeter containing the first space spanning an interior space and excluding the second space comprising the exterior space;
within the map, identifying the door between the first space and the second space and proximal a boundary of the first individual access perimeter; and
setting a flag to trigger the door to enter the locked state in the presence of any resident wearable device assigned to the first resident during the first period of time; and
wherein triggering the door to enter the locked state comprises triggering the door to enter the locked state in response to proximity of the first resident wearable device to the door when the flag is active during the first period of time.

6. The method of claim 5, further comprising disabling the flag in response to activation of an emergency alarm within the facility.

7. The method of claim 1, wherein defining the first individual access perimeter comprises:
accessing a characteristic of the first resident from a resident profile associated with the first resident;
incorporating the first space, spanning a public common space within the facility, into the first individual access perimeter; and
excluding the second space from the first individual access perimeter based on a predefined rule for supervision of residents exhibiting the characteristic when occupying the second space.

8. The method of claim 7:
wherein accessing the characteristic of the first resident comprises identifying the first resident as diagnosed with dementia based on an electronic health record of the first resident;
wherein excluding the second space from the first individual access perimeter comprises excluding an exercise space within the facility from the first individual access perimeter based on the predefined rule for supervision of residents exhibiting dementia when occupying the exercise space;
wherein maintaining the door in the unlocked state by default during the first period of time comprises maintaining the door between the public common space and the exercise space in the unlocked state by default during an open exercise period in the exercise space;
further comprising tracking locations of care provider mobile devices associated with care providers affiliated with the facility; and
wherein triggering the door to enter the locked state comprises triggering the door to enter the locked state in response to the first location of the first resident wearable device falling within the threshold distance of the door during the open exercise period while the exercise space is vacant of care provider mobile devices.

9. The method of claim 1, further comprising:
in response to a second location of a second resident wearable device associated with a second resident, in the set of residents, falling outside of the generic access perimeter, assigned to the second resident, at a second time, distributing a first breach event prompt to assist the second resident proximal the second location to care provider mobile devices associated with care providers affiliated with the facility; and
in response to a third location of the first resident wearable device falling outside of the first individual access perimeter at a third time, distributing a second breach event prompt to assist the first resident, proximal the third location, to care provider mobile devices associated with care providers affiliated with the facility.

10. The method of claim 1:
wherein tracking locations of resident wearable devices within the facility comprises tracking locations of the first resident wearable device based on wireless communications between the first resident wearable device and a set of wireless communication hubs distributed throughout the facility;
further comprising, in response to an initial location of the first resident wearable device falling within the first individual access perimeter and in response to the first resident wearable device approaching a boundary of the first individual access perimeter at an initial time preceding the third time, distributing a perimeter observation prompt for the first resident to care provider mobile devices within the facility, the perimeter observation prompt indicating the initial location of the first resident and comprising a prompt to observe the first resident; and
wherein distributing the third breach event prompt comprises distributing the third breach event prompt to care provider mobile devices within the facility in response to the first resident wearable device moving beyond the boundary of the first individual access perimeter at approximately the third time.

11. The method of claim 1:
wherein tracking locations of resident wearable devices within the facility comprises tracking locations of the first resident wearable device based on wireless communications between the first resident wearable device and a set of wireless communication hubs distributed throughout the facility;
further comprising confirming proximity of the first resident wearable device to the door based on wireless communications between the first resident wearable device and a wireless unit arranged at the door; and
wherein triggering the door to enter the locked state comprises triggering the door to enter the locked state in response to communications between the first resident wearable device and the wireless unit confirming proximity of the first resident wearable device to the door.

12. The method of claim 1, further comprising:
calculating a speed of the first resident during the first period of time based on detected locations of the first resident wearable device; and
setting the threshold distance proportional to the speed of the first resident.

13. The method of claim 1, further comprising:
tracking locations of a set of care provider mobile devices associated with care providers affiliated with the facility; and
in response to a first care provider mobile device, in the set of care provider mobile devices, occupying the second space and within a preset supervising distance of the door, maintaining the door in the unlocked state when the first resident wearable device falls inside the threshold distance of the door.

14. The method of claim 1, further comprising:
tracking locations of an access pass activated for a visitor of the first resident; and
in response to the access pass and the first resident wearable device falling within a preset supervising distance and moving together toward the door, maintaining the door in the unlocked state as the access pass and the first resident wearable device approach and pass through the door.

15. The method of claim 1, further comprising:
in response to triggering the door to enter the locked state, transmitting a notification to a care provider mobile device proximal the door, the notification indicating transition of the door into the locked state responsive to proximity of the first resident; and
in response to selection of an override command at the care provider wearable device, triggering the door to return to the unlocked state.

16. The method of claim 1, further comprising:
at the first resident wearable device:
scanning a position sensor integrated into the resident wearable device for changes in position of the resident wearable device;
scanning a temperature sensor integrated into the resident wearable device for temperatures of an adjacent surface;
confirming presence of the first resident wearable device on the first resident responsive to frequent changes in position of the resident wearable device and temperatures, read by the temperature sensor, falling within a threshold range; and
detecting removal of the first resident wearable device from the first resident responsive to infrequent changes in position of the resident wearable device and temperatures, read by the temperature sensor, falling outside of the threshold range;
storing a last location of the first resident wearable device corresponding to confirmation of presence of the first resident wearable device on the first resident; and
issuing a prompt to assist the first resident, proximal the last location, to care provider mobile devices associated with care providers affiliated with the facility in response to detection of removal of the first resident wearable device from the first resident.

17. A method for controlling access within an assisted living facility comprising:
defining an access perimeter containing a first space and excluding a second space within a facility, the first space and the second space separated by a door;
assigning the first individual access perimeter to a first resident, in a set of residents, occupying the facility;
maintaining the door in an unlocked state by default during a first period of time;
tracking locations of resident wearable devices associated with residents, in the set of residents, within the facility during the first period of time;
in response to a first location of a first resident wearable device associated with the first resident falling inside the individual access perimeter and within a threshold distance of the door at a first time during the first period of time, triggering the door to enter a locked state; and
in response to the first resident wearable device moving outside of the threshold distance of the door at a second time succeeding the first time, triggering the door to return to the unlocked state.

18. The method of claim 17:
wherein defining the access perimeter comprises defining the access perimeter:
containing the first space spanning a public space within the facility; and
excluding the second space spanning a private room assigned to a second resident in the facility; and
wherein triggering the door to enter the locked state comprises triggering the door to enter the locked state in response to the first resident wearable device occupying the public space within the threshold distance of the private room while a second resident wearable device associated with the second resident is absent from the private room.

19. The method of claim 17, further comprising:
further comprising tracking locations of care provider mobile devices associated with care providers affiliated with the facility; and
in response to a first care provider mobile device falling within a second threshold distance of the door less than the threshold distance, maintaining the door in the unlocked state when the first resident wearable device falls within the threshold distance of the door.

20. The method of claim 17, further comprising:
in response to a second location of the first resident wearable device falling outside of the access perimeter at a second time, distributing a breach event prompt to assist the first resident, proximal the second location, to a set of care provider mobile devices associated with care providers active in the facility during the first period of time;
in response to receipt of a breach event confirmation from a first care provider mobile device, in the set of care provider mobile devices, deescalating the breach event prompt at a second care provider mobile device within the set of care provider mobile devices; and
in response to confirmation of the first care provider mobile device proximal the first resident wearable device, authorizing edit permissions for an electronic incident report by a first care provider associated with the first care provider mobile device exclusive of a second care provider associated with the second care provider mobile device.

* * * * *